United States Patent
Brumback et al.

(10) Patent No.: US 9,042,971 B2
(45) Date of Patent: May 26, 2015

(54) BIOMETRIC MONITORING DEVICE WITH HEART RATE MEASUREMENT ACTIVATED BY A SINGLE USER-GESTURE

(71) Applicant: Fitbit, Inc., San Francisco, CA (US)

(72) Inventors: Christine Boomer Brumback, San Francisco, CA (US); Nicholas Adrian Myers, Oakland, CA (US); Shelten Gee Jao Yuen, Berkeley, CA (US); James Park, Berkeley, CA (US); Todd Sutham Diemer, Oakland, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/154,009

(22) Filed: Jan. 13, 2014

(65) Prior Publication Data

US 2014/0135631 A1 May 15, 2014

Related U.S. Application Data

(63) Continuation-in-part of application No. 13/924,784, filed on Jun. 24, 2013.

(60) Provisional application No. 61/662,961, filed on Jun. 22, 2012, provisional application No. 61/752,826, filed on Jan. 15, 2013, provisional application No. 61/830,600, filed on Jun. 3, 2013.

(51) Int. Cl.
*A61B 5/04* (2006.01)
*A61B 5/024* (2006.01)
(Continued)

(52) U.S. Cl.
CPC ......... *A61B 5/02427* (2013.01); *A61B 5/02438* (2013.01); *A61B 5/11* (2013.01);
(Continued)

(58) Field of Classification Search
CPC .. A61B 5/02427; A61B 5/02438; A61B 5/11; A61B 5/681; A61B 5/02055; A61B 5/4809; H04W 84/12; H04L 67/12
USPC .......... 340/576; 600/407, 365, 595, 300, 309, 600/340, 509, 510, 521
See application file for complete search history.

(56) References Cited

U.S. PATENT DOCUMENTS

| 4,367,752 A | 1/1983 | Jimenez et al. |
| 4,771,792 A | 9/1988 | Seale |

(Continued)

FOREIGN PATENT DOCUMENTS

EP  1 721 237  8/2012

OTHER PUBLICATIONS

U.S. Appl. No. 13/924,784, filed Jun. 24, 2013, Yuen et al.
(Continued)

*Primary Examiner* — Unsu Jung
*Assistant Examiner* — Joel Lamprecht
(74) *Attorney, Agent, or Firm* — Weaver Austin Villeneuve & Sampson LLP

(57) ABSTRACT

A biometric monitoring device measuring various biometric information is provided that allows the person to take and/or display a heart rate reading by a simple user interaction with the device, e.g., by simply touching a heart rate sensor surface area or moving the device in a defined motion pattern. Some embodiments of this disclosure provide biometric monitoring devices that allow a person to get a quick heart rate reading without removing the device or interrupting their other activities. Some embodiments provide heart rate monitoring with other desirable features such as feedback on data acquisition status.

28 Claims, 17 Drawing Sheets

(51) Int. Cl.
*A61B 5/11* (2006.01)
*A61B 5/00* (2006.01)
*H04L 29/08* (2006.01)
*H04W 4/00* (2009.01)
*A61B 5/0205* (2006.01)
*H04W 84/12* (2009.01)

(52) U.S. Cl.
CPC ............... *A61B 5/681* (2013.01); *H04W 4/008* (2013.01); *A61B 5/02055* (2013.01); *A61B 5/4809* (2013.01); *H04W 84/12* (2013.01); *H04L 67/12* (2013.01)

(56) References Cited

U.S. PATENT DOCUMENTS

| | | | |
|---|---|---|---|
| 5,036,856 A | 8/1991 | Thornton | |
| 5,101,831 A | 4/1992 | Koyama et al. | |
| 5,318,597 A | 6/1994 | Hauck et al. | |
| 5,738,104 A * | 4/1998 | Lo et al. | 600/521 |
| 6,131,076 A | 10/2000 | Stephan et al. | |
| 6,241,684 B1 | 6/2001 | Amano et al. | |
| 6,418,394 B1 | 7/2002 | Puolakanaho et al. | |
| 6,583,369 B2 | 6/2003 | Montagnino et al. | |
| 6,720,860 B1 | 4/2004 | Narayanaswami | |
| 6,731,967 B1 | 5/2004 | Turcott | |
| 6,997,882 B1 | 2/2006 | Parker et al. | |
| 7,539,532 B2 * | 5/2009 | Tran | 600/509 |
| 7,720,306 B2 | 5/2010 | Gardiner et al. | |
| 8,040,758 B1 | 10/2011 | Dickinson | |
| 8,152,745 B2 | 4/2012 | Smith et al. | |
| 8,211,503 B2 | 7/2012 | Tsao et al. | |
| 8,346,328 B2 | 1/2013 | Mannheimer et al. | |
| 8,386,042 B2 | 2/2013 | Yudovsky et al. | |
| 8,444,578 B2 | 5/2013 | Bourget et al. | |
| 8,475,367 B1 | 7/2013 | Yuen et al. | |
| 8,579,827 B1 | 11/2013 | Rulkov et al. | |
| 8,792,981 B2 | 7/2014 | Yudovsky et al. | |
| 8,920,332 B2 | 12/2014 | Hong et al. | |
| 8,945,017 B2 | 2/2015 | Venkatraman et al. | |
| 8,948,832 B2 | 2/2015 | Hong et al. | |
| 8,954,135 B2 | 2/2015 | Yuen et al. | |
| 8,956,303 B2 | 2/2015 | Hong et al. | |
| 8,998,815 B2 | 4/2015 | Venkatraman et al. | |
| 9,005,129 B2 | 4/2015 | Venkatraman et al. | |
| 2001/0044588 A1 | 11/2001 | Mault | |
| 2003/0163710 A1 | 8/2003 | Ortiz et al. | |
| 2004/0236227 A1 | 11/2004 | Gueissaz | |
| 2005/0054940 A1 * | 3/2005 | Almen | 600/509 |
| 2005/0245793 A1 | 11/2005 | Hilton et al. | |
| 2006/0195020 A1 | 8/2006 | Martin et al. | |
| 2008/0097221 A1 | 4/2008 | Florian | |
| 2008/0249836 A1 | 10/2008 | Angell et al. | |
| 2009/0012433 A1 | 1/2009 | Fernstrom et al. | |
| 2010/0106044 A1 | 4/2010 | Linderman | |
| 2010/0152600 A1 | 6/2010 | Droitcour et al. | |
| 2010/0249633 A1 | 9/2010 | Droitcour et al. | |
| 2010/0292568 A1 | 11/2010 | Droitcour et al. | |
| 2010/0298650 A1 | 11/2010 | Moon et al. | |
| 2010/0298651 A1 | 11/2010 | Moon et al. | |
| 2010/0298653 A1 | 11/2010 | McCombie et al. | |
| 2010/0298661 A1 | 11/2010 | McCombie et al. | |
| 2010/0331145 A1 | 12/2010 | Lakovic et al. | |
| 2010/0331657 A1 * | 12/2010 | Mensinger et al. | 600/365 |
| 2011/0009727 A1 * | 1/2011 | Mensinger et al. | 600/365 |
| 2011/0032105 A1 | 2/2011 | Hoffman et al. | |
| 2011/0066010 A1 | 3/2011 | Moon et al. | |
| 2012/0083705 A1 | 4/2012 | Yuen et al. | |
| 2012/0083714 A1 | 4/2012 | Yuen et al. | |
| 2012/0083715 A1 | 4/2012 | Yuen et al. | |
| 2012/0083716 A1 | 4/2012 | Yuen et al. | |
| 2012/0084053 A1 | 4/2012 | Yuen et al. | |
| 2012/0084054 A1 | 4/2012 | Yuen et al. | |
| 2012/0123232 A1 | 5/2012 | Najarian et al. | |
| 2012/0150074 A1 | 6/2012 | Yanev et al. | |
| 2012/0172733 A1 | 7/2012 | Park | |
| 2012/0226471 A1 | 9/2012 | Yuen et al. | |
| 2012/0226472 A1 | 9/2012 | Yuen et al. | |
| 2012/0232432 A1 | 9/2012 | Kahn et al. | |
| 2012/0245439 A1 | 9/2012 | Andre et al. | |
| 2012/0255875 A1 | 10/2012 | Vicente et al. | |
| 2012/0274508 A1 | 11/2012 | Brown et al. | |
| 2012/0316471 A1 * | 12/2012 | Rahman et al. | 600/595 |
| 2013/0009779 A1 * | 1/2013 | Wittling et al. | 340/576 |
| 2013/0073254 A1 | 3/2013 | Yuen et al. | |
| 2013/0073255 A1 | 3/2013 | Yuen et al. | |
| 2013/0077826 A1 | 3/2013 | Cowperthwaite et al. | |
| 2013/0080113 A1 | 3/2013 | Yuen et al. | |
| 2013/0106684 A1 | 5/2013 | Weast et al. | |
| 2013/0151196 A1 | 6/2013 | Yuen et al. | |
| 2013/0158369 A1 | 6/2013 | Yuen et al. | |
| 2013/0163390 A1 | 6/2013 | Gossweiler, III et al. | |
| 2013/0211265 A1 | 8/2013 | Bedingham et al. | |
| 2013/0218053 A1 | 8/2013 | Kaiser et al. | |
| 2013/0280682 A1 | 10/2013 | Levine et al. | |
| 2014/0073486 A1 | 3/2014 | Ahmed et al. | |
| 2014/0099614 A1 | 4/2014 | Hu et al. | |
| 2014/0107493 A1 | 4/2014 | Yuen et al. | |
| 2014/0142403 A1 | 5/2014 | Brumback et al. | |
| 2014/0241626 A1 | 8/2014 | Sull et al. | |
| 2014/0275821 A1 | 9/2014 | Beckman | |
| 2014/0275852 A1 | 9/2014 | Hong et al. | |
| 2014/0275854 A1 | 9/2014 | Venkatraman et al. | |
| 2014/0276119 A1 | 9/2014 | Venkatraman et al. | |
| 2014/0278139 A1 | 9/2014 | Hong et al. | |
| 2014/0288390 A1 | 9/2014 | Hong et al. | |
| 2014/0288391 A1 | 9/2014 | Hong et al. | |
| 2014/0288392 A1 | 9/2014 | Hong et al. | |
| 2014/0288435 A1 | 9/2014 | Richards et al. | |
| 2014/0288436 A1 | 9/2014 | Venkatraman et al. | |
| 2014/0288438 A1 | 9/2014 | Venkatraman et al. | |
| 2014/0303523 A1 | 10/2014 | Hong et al. | |
| 2015/0025393 A1 | 1/2015 | Hong et al. | |
| 2015/0025394 A1 | 1/2015 | Hong et al. | |

OTHER PUBLICATIONS

U.S. Appl. No. 14/073,657, filed Nov. 6, 2013, Park et al.
U.S. Appl. No. 14/073,702, filed Nov. 6, 2013, Park et al.
U.S. Appl. No. 14/154,019, filed Jan. 13, 2014, Brumback et al.
US Office Action, dated Mar. 13, 2014, issued in U.S. Appl. No. 14/073,657.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior.html], 10 pp.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
Cooper, Daniel (Aug. 16, 2013) *Withings Pulse review*, http://www.engadget.com/2013/08/16/withings-pulse-revew/, 8 pages.
DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch With Wireless Sync," (Mar. 2009), Garmin Ltd., 56 pp.

(56) References Cited

OTHER PUBLICATIONS

Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Larklife, User Manual, (2012) Lark Technologies, 7 pp.
Lark/Larkpro, User Manual, (2012) "What's in the box," Lark Technologies, 7 pp.
LifeTrnr, User Manual (2003, specific date unknown), NB new balance®, Implus Footcare, LLC, 3 pages.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TomTom, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, POLAR® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Rainmaker, (Jul. 25, 2013) "Basis $B_1$ Watch In-Depth Review," [retrieved on Feb. 4, 2014 at http://www.dcrainmaker.com/2013/07/basis-b1-review.html], 56 pp.
"Withings pulse, Quick Installation Guide" (Jul. 24, 2013) Withings Pulse QIG, v 1.3, withings.com/pulse, 16 pages.
U.S. Appl. No. 14/214,655, filed Mar. 14, 2014, Hong et al.
U.S. Appl. No. 14/481,020, filed Sep. 9, 2014, Hong et al.
U.S. Appl. No. 14/481,762, filed Sep. 9, 2014, Hong et al.
U.S. Appl. No. 14/484,104, filed Sep. 11, 2014, Brumback et al.
U.S. Appl. No. 14/507,173, filed Oct. 6, 2014, Hong et al.
U.S. Appl. No. 14/507,184, filed Oct. 6, 2014, Hong et al.
US Office Action, dated Aug. 4, 2014, issued in U.S. Appl. No. 13/924,784.
US Notice of Allowance, dated Nov. 19, 2014, issued in U.S. Appl. No. 13/924,784.
US Office Action, dated Oct. 22, 2014, issued in U.S. Appl. No. 14/290,884.
US Notice of Allowance, dated Sep. 23, 2014, issued in U.S. Appl. No. 14/292,669.
US Notice of Allowance (Corrected Notice of Allowability), dated Oct. 14, 2014, issued in U.S. Appl. No. 14/292,669.
US Notice of Allowance, dated Oct. 14, 2014, issued in U.S. Appl. No. 14/295,144.
US Notice of Allowance, dated Dec. 3, 2014, issued in U.S. Appl. No. 14/295,144.
US Notice of Allowance, dated Sep. 26, 2014, issued in U.S. Appl. No. 14/295,158.
US Office Action, dated Aug. 5, 2014, issued in U.S. Appl. No. 14/292,673.
US Notice of Allowance, dated Dec. 8, 2014, issued in U.S. Appl. No. 14/292,673.
US Office Action, dated Sep. 18, 2014, issued in U.S. Appl. No. 14/295,059.
US Office Action, dated Jul. 31, 2014, issued in U.S. Appl. No. 14/295,122.
US Notice of Allowance, dated Nov. 24, 2014, issued in U.S. Appl. No. 14/295,122.
US Office Action, dated Nov. 25, 2014, issued in U.S. Appl. No. 14/154,019.
US Office Action, dated Dec. 10, 2014, issued in U.S. Appl. No. 14/484,104.
US Office Action, dated Dec. 4, 2014, issued in U.S. Appl. No. 14/216,743.
US Office Action, dated Aug. 22, 2014, issued in U.S. Appl. No. 14/250,256.
US Final Office Action, dated Nov. 21, 2014, issued in U.S. Appl. No. 14/250,256.
US Office Action, dated Oct. 7, 2014, issued in U.S. Appl. No. 14/481,762.
Zijlstra, Wiebren, (2004) "Assessment of spatio-temporal parameters during unconstrained walking," Eur J Appl Physiol, 92:39-44.
U.S. Appl. No. 14/599,039, filed Jan. 16, 2015, Venkatraman et al.
US Notice of Allowance, dated Feb. 6, 2015, issued in U.S. Appl. No. 14/290,884.
US Notice of Allowance (Corrected Notice of Allowability), dated Dec. 31, 2014, issued in U.S. Appl. No. 14/292,669.
US Notice of Allowance (Corrected Notice of Allowability), dated Dec. 31, 2014, issued in U.S. Appl. No. 14/295,158.
US Office Action, dated Jan. 23, 2015, issued in U.S. Appl. No. 14/507,184.
US Office Action, dated Jan. 26, 2015, issued in U.S. Appl. No. 14/295,161.
US Office Action, dated Jan. 27, 2015, issued in U.S. Appl. No. 14/507,173.
US Notice of Allowance (Corrected Notice of Allowability), dated Mar. 5, 2015, issued in U.S. Appl. No. 14/292,673.
US Notice of Allowance, dated Jan. 28, 2015, issued in U.S. Appl. No. 14/295,059.
US Notice of Allowance (Corrected Notice of Allowability), dated Mar. 11, 2015, issued in U.S. Appl. No. 14/295,059.
US Notice of Allowance (Corrected Notice of Allowability), dated Jan. 5, 2015, issued in U.S. Appl. No. 14/295,122.
US Notice of Allowance, dated Mar. 20, 2015, issued in U.S. Appl. No. 14/154,019.
US Notice of Allowance, dated Mar. 19, 2015, issued in U.S. Appl. No. 14/484,104.
US Office Action, dated Mar. 12, 2015, issued in U.S. Appl. No. 14/481,020.
U.S. Appl. No. 14/673,630, filed Mar. 30, 2015, Hong et al.
U.S. Appl. No. 14/673,634, filed Mar. 30, 2015, Hong et al.
US Notice of Allowance, dated Apr. 14, 2015, issued in U.S. Appl. No. 14/295,161.
US Final Office Action, dated Apr. 15, 2015, issued in U.S. Appl. No. 14/295,076.
US Final Office Action, dated Apr. 8, 2015, issued in U.S. Appl. No. 14/216,743.

\* cited by examiner

BIOMETRIC MONITORING DEVICE WITH HEART RATE MEASUREMENT ACTIVATED BY A SINGLE USER-GESTURE

CROSS REFERENCE TO RELATED APPLICATIONS

This application is a continuation-in-part of U.S. application Ser. No. 13/924,784, filed Jun. 24, 2013, which claims the benefit under 35 U.S.C. §119(e)(1) of both U.S. Provisional Patent Application No. 61/662,961, filed Jun. 22, 2012, and U.S. Provisional Patent Application No. 61/752,826, filed Jan. 15, 2013; this application also claims the benefit under 35 U.S.C. §119(e)(1) of U.S. Provisional Patent Application No. 61/830,600, filed Jun. 3, 2013. The above-listed applications are hereby incorporated by reference in their entirety.

BACKGROUND

Recent advances in sensor, electronics, and power source miniaturization have allowed the size of personal health monitoring devices, also referred to herein as "biometric tracking" or "biometric monitoring" devices, to be offered in small sizes. These biometric monitoring devices may collect, derive, and/or provide one or more of the following types of information: heart rate, calorie burn, floors climbed and/or descended, location and/or heading, elevation, ambulatory speed and/or distance traveled, etc. One piece of useful physiological information measured by biometric monitoring devices relates to heart rate. As biometric monitoring devices are trending to integrate multiple sensors to measure various types of physiological and environmental information, existing devices that measure momentary heart rate require cumbersome user interaction to take the measurement, display the measured information and/or provide other user feedback. This disclosure provides biometric monitoring devices with convenient and user-friendly heart rate monitoring function.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some embodiments, the device provides user feedback regarding the collected heart rate data without requiring further user input beyond activating the heart rate sensor. Heart rate monitoring activated by a single user-gesture is desirable. For instance, a single touch of the activator surface area can provide a signal to activate the heart rate sensor without requiring any other user input. This is advantageous because it simplifies the process to activate a heart rate sensor from an off state to an on state. It is desirable to activate the sensor on demand, because it reduces energy consumption compared to continual, continuous, or regularly intermittent activation. The present inventors have realized that this energy conservation is important for portable devices with multiple functions and miniaturized size. Furthermore, the present inventors have realized that it is desirable to activate the sensor using only a single user-gesture as opposed to multiple gestures, e.g., separate gestures to turn on the heart rate sensor, start heart rate data collection, provide user feedback based on heart rate data. The simplification of the process to obtain a heart rate measure and/or providing feedback allows users to obtain heart rate measurement and/or receive feedback under circumstances that are otherwise impossible, impractical, or inconvenient to obtain the measure and/or receive the feedback.

In some implementations, an apparatus is provided as a biometric monitoring device with heart rate measuring function activated by a single user-gesture. The apparatus may include: one or more biometric sensors comprising a heart rate sensor, an activator of the heart rate sensor, a heart rate sensor surface area through which the heart rate sensor can collect heart rate data from a user, an activator surface area through which the activator can receive activation signals from the user, at least one processor, and a memory. In these implementations, the one or more biometric sensors, the activator, the at least one processor, and the memory are communicatively connected. Furthermore, the memory stores computer-executable instructions for controlling the at least one processor to cause the heart rate sensor to start collecting heart rate data through the heart rate sensor surface area in response to the activator receiving an activation signal through the activator surface area caused by a single user-gesture. Additionally, the heart rate sensor is configured to automatically stop collecting heart rate data after a defined criterion is met and remain in a state that does not collect heart rate data until another activation signal caused by a new user-gesture is received without requiring further user-gestures in addition to the single user-gesture. In some embodiments, the defined criterion is a defined period of time for heart rate data collection or a defined quality of heart rate reading.

In some implementations, a different biometric monitoring device is provided in an apparatus. In these embodiments, compared to the embodiments described above, the apparatus comprises an optical heart rate sensor instead of a general heart rate sensor, and the apparatus additionally includes a feedback mechanism. In these embodiments, the optical heart rate sensor, the activator, the at least one processor, and the memory are communicatively connected. The memory stores computer-executable instructions for controlling the at least one processor to cause the optical heart rate sensor to start collecting heart rate data through the heart rate sensor surface area in response to the activator receiving an activation signal through the activator surface area caused by a single user-gesture. Furthermore, the apparatus is configured to provide user feedback, through the feedback mechanism, with reference to the collected heart rate data without requiring further user-gestures in addition to the single user-gesture.

In some embodiments, the biometric monitoring device further includes an altimeter communicatively connected with the heart rate sensor, the activator, the at least one processor, and the memory. The memory further stores computer-executable instructions for controlling the at least one processor to obtain altitude data from the altimeter.

In some embodiments, the heart rate sensor is configured to only collect data when the single user-gesture is occurring and only from a body part of the user used to provide the single user-gesture.

In some embodiments, the heart rate sensor surface area and the activator surface area are arranged on a substantially flat plane, thereby allowing a single body part of a user to simultaneously interact with the activator and the heart rate sensor.

In some embodiments, the memory further stores computer-executable instructions for controlling the at least one processor to cause the heart rate sensor to stop collecting heart rate data after a defined criterion is met without requiring further user gestures in addition to the single user-gesture.

In some embodiments, the apparatus further comprises a vibration motor as a feedback mechanism and the feedback to the user is provided as haptic vibration.

In some embodiments, the apparatus further comprises a housing that houses at least the heart rate sensor and the activator. The heart rate sensor surface area and the activator surface area are on located on the housing. In various embodiments, they are less than about 2, 1, 0.5, 0.2, or 0.1 centimeters apart as measured by the distance along the exterior surface of the housing. This design allows a single body part of a user to simultaneously interact with the activator and the heart rate sensor. In some embodiments, the heart rate sensor surface area and the activator surface area overlap along the exterior surface of the housing. In some embodiments, the heart rate sensor surface area and/or the activator surface area is a seamless portion of the surface of the housing. In some embodiments, the apparatus has only one heart rate sensor surface area. In other embodiments, the apparatus has two or more heart rate sensor surface areas. In some embodiments, the heart rate sensor surface area and the activator surface area form one continuous surface area.

In some embodiments, the activator of the heart rate sensor is a proximity sensor. In some embodiments, the single user-gesture providing the activation signal to the heart rate sensor activator consists of the user bringing a body part into proximity with the activator surface area.

In some embodiments, the single user-gesture consists of a touch of the activator surface area using a single body part.

In some embodiments, the apparatus is configured to be removably attachable to a wearable accessory, and the activator surface area and heart rate sensor surface area are configured to be accessible for user interaction when attached to the wearable accessory.

In some embodiments, the heart rate sensor, the activator, the at least one processor, and the memory are communicatively connected to a user interface on the apparatus. In some embodiments, the heart rate sensor, the activator, the at least one processor, and the memory are communicatively connected to a user interface on a linked smartphone, tablet, or computer. In some embodiments, the user interface includes one or more of the following: the heart rate sensor surface area, the activator surface area, a touch screen, a display, an LED, a button, an accelerometer, a gyroscope, a finger print reader, a vibration motor, a proximity sensor, and a speaker.

In some implementations, an apparatus is provided as a biometric monitoring device with heart rate measuring function activated by a single user-gesture. The apparatus may include: two or more biometric sensors comprising a heart rate sensor and an altimeter, an activator of the heart rate sensor, a heart rate sensor surface area through which the heart rate sensor can collect heart rate data from a user, at least one processor, and a memory. The heart rate sensor, the altimeter, the activator, the at least one processor, and the memory are communicatively connected. The memory stores computer-executable instructions for controlling the at least one processor to cause the heart rate sensor to start collecting heart rate data through the heart rate sensor surface area in response to the activator receiving an activation signal caused by a single user-gesture. In some implementations, the memory further stores computer-executable instructions for controlling the at least one processor to obtain altitude data from the altimeter. In some implementations, the altitude data includes atmosphere pressure data or environmental pressure data, or relative changes thereof.

In some implementations, biometric monitoring device includes a heart rate sensor and an electromyographic sensor, a heart rate sensor surface area, at least one processor, and a memory. The heart rate sensor, the electromyographic sensor, the at least one processor, and the memory are communicatively connected. The memory stores computer-executable instructions for controlling the at least one processor to cause the heart rate sensor to start collecting heart rate data through the heart rate sensor surface area in response to the electromyographic sensor receiving an activation signal caused by a single user-gesture. In some implementations, the single user-gesture includes clenching the first of the hand wearing the apparatus. In some implementations, the device is configured to provide user feedback with reference to the collected heart rate data without requiring further user-gesture in addition to the single user-gesture.

In some implementations, an apparatus is provided as a biometric monitoring device with heart rate measuring function activated by a single user-gesture. The apparatus may include: one or more biometric sensors comprising an optical heart rate sensor, an activator of the optical heart rate sensor, a heart rate sensor surface area through which the optical heart rate sensor can collect heart rate data from a user, a feedback mechanism, at least one processor, and a memory. The optical heart rate sensor, the activator, the feedback mechanism, the at least one processor, and the memory are communicatively connected. In some implementations, instead of or in addition to local memory, the apparatus communicatively connects with a memory remotely linked to the apparatus, such as a memory on a server computer or a smart phone. The memory stores computer-executable instructions for controlling the at least one processor to cause the optical heart rate sensor to start collecting heart rate data through the heart rate sensor surface area in response to the activator receiving an activation signal caused by a single user-gesture. The device is configured to provide user feedback, through the feedback mechanism, with reference to the collected heart rate data without requiring further user-gestures in addition to the single user-gesture.

In some implementations, the optical heart rate sensor is configured to automatically stop collecting heart rate data after a defined criterion is met without requiring further user gestures in addition to the single user-gesture. In some implementations, the optical heart rate sensor is configured to, after it stops collecting heart rate data, remain in a state that does not collect heart rate data until another activation signal caused by a new user-gesture is received.

In some implementations, the activator comprises at least one sensor includes one or more of single-axis or multi-axis gyroscopes and/or single-axis or multi-axis accelerometers. The single user-gesture consists of a user moving or interacting with the apparatus in a defined motion pattern. The memory further stores computer-executable instructions for controlling the at least one processor to cause the optical heart rate sensor to start collecting heart rate data in response to a detection of the defined motion pattern using data obtained by the activator. In some implementations, moving or interacting with the apparatus in a defined motion pattern is selected from one or more of the following: twisting the wrist wearing the apparatus, shaking the apparatus, bringing a wrist wearing the apparatus from a resting position to a watch-viewing position, moving the apparatus in a "figure 8" motion, and any combinations thereof. In some implementations, the apparatus is configured to be wearable as a wrist-band.

In some implementations, the feedback to the user with reference to the collected heart rate data includes one or more of the following: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate. In some implementations, the apparatus is configured to automatically authenticate the user based on the collected heart rate data.

In some implementations, the optical heart rate sensor comprises an optical heart rate sensor for the visible light spectrum. In some implementations, the optical heart rate sensor comprises an optical heart rate sensor for infrared light. In some implementations, the optical heart rate sensor comprises a photoplethysmograph (PPG) sensor or pulse oximetry sensor.

In some implementations, the one or more biometric sensors further includes one or more of the following: GPS, proximity sensor, gyroscope, magnetometer, accelerometer, ambient light sensor, touch screen, temperature sensor, galvanic skin response sensor, fingerprint reader, electromyographic sensor, altimeter, pressure transducer, and force transducer, audio sensor, bioelectrical impedance sensor, blood pressure sensor, moisture sensor, and blood glucose sensor. In some implementations, the apparatus includes a motion sensor providing motion data to compensate for disruptions caused by arm movements that would otherwise interfere with the heart rate data. In some implementations, the apparatus has two or more heart rate sensors.

In some implementations, the apparatus has feedback mechanism including a display. The feedback to the user is provided as a visual feedback through the display. In some implementations, the visual feedback through the display includes causing the display and/or a display backlight to turn on from an off or standby state.

In some implementations, the apparatus is configured to show, through the feedback mechanism, information derived from one or more of the following with or without further user input: calorie burn, floors climbed and/or descended, location and/or heading, elevation, ambulatory speed and/or distance traveled, swimming lap count, bicycle distance and/or speed, blood pressure, blood glucose, skin conduction, skin and/or body temperature, electromyography data, electroencephalography data, weight, body fat, caloric intake, nutritional intake from food, medication intake, sleep periods, sleep phases, sleep quality and/or duration, pH levels, hydration levels, and respiration rate, barometric pressure, temperature, humidity, pollen count, air quality, rain/snow conditions, wind speed, ambient light, UV light exposure, time and/or duration spent in darkness, noise exposure, radiation exposure, and magnetic field.

In some embodiments, the apparatus is configured to provide feedback indicating that heart rate collection has started, succeeded, ended, and/or failed.

In some embodiments, a method for monitoring heart rate using a biometric monitoring device is provided. In some embodiments, the method involves receiving, by an activator, an activation signal representing a single user-gesture by a user. The method further involves activating a heart rate sensor, in response to the activation signal, to start collecting heart rate data from the user. The method also involves providing user feedback, through a feedback mechanism, with reference to the collected heart rate data without requiring further user-gestures in addition to the single user-gesture. In some embodiments, the user feedback is provided by haptic vibration. In some embodiments, the user feedback includes an indication that heart rate data collection is successful and/or an indication that heart rate data collection has failed. In some embodiments, the user feedback includes one or more of the following: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate.

In some embodiments, the method additionally involves causing the heart rate sensor to stop collecting heart rate data after a defined criterion is met without requiring further user-gestures in addition to the single user-gesture. In some embodiments, the method further includes causing the heart rate sensor to remain in a state that does not collect heart rate data until another activation signal caused by a new user-gesture is received.

In some embodiments, the heart rate sensor only collects data when the single user-gesture is occurring and from a body part of the user used to provide the single user-gesture. In some embodiments, the defined criterion relates to a time period of heart rate data collection and/or quality of heart rate data collected.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Introduction

Previously available biometric monitoring devices (BMDs) (also referred to herein as "biometric tracking devices" or simply as "devices") capable of measuring various types of information tend to use cumbersome approaches to gather and provide the information. For instance, a biometric monitoring device (BMD) may require a user to interrupt what she is doing to take or display a heart rate measurement. It is desirable to have heart rate measuring devices that require minimal involvement by user in order to obtain on-demand HR measurement. Such devices allow the person to take and/or display a heart rate reading by a simple user interaction with the device, e.g., by simply touching a heart rate sensor surface area. Some embodiments of this disclosure provide biometric monitoring devices that allow a person to get a quick heart rate reading without removing the device or interrupting their other activities. Some embodiments provide heart rate monitoring with other desirable features. In some implementations, the biometric monitoring device (BMD) provides heart rate monitoring functions that are user friendly and simple to perform. In some implementations, a single user-gesture causes the device to collect heart rate data. In some embodiments, a single user-gesture also causes the device to provide feedback to a user with regard to the heart rate data. Various embodiments with heart rate monitoring functions activated by a single user-gesture are further described herein after.

In some implementations, a biometric monitoring device may be designed such that it may be inserted into, and removed from, a plurality of compatible cases/housings/holders, e.g., a wristband that may be worn on a person's forearm or a belt clip case that may be attached to a person's clothing. In some embodiments, the biometric monitoring system may also include other devices or components communicatively linked to the biometric monitoring device. The communicative linking may involve direct or indirect connection, as well as wired and wireless connections. Components of said system may communicate to one another over a wireless connection (e.g. Bluetooth) or a wired connection (e.g. USB). Indirect communication refers to the transmission of data between a first device and a secondary device with the aid of one or multiple intermediary third devices which relay the data.

Figure 1:
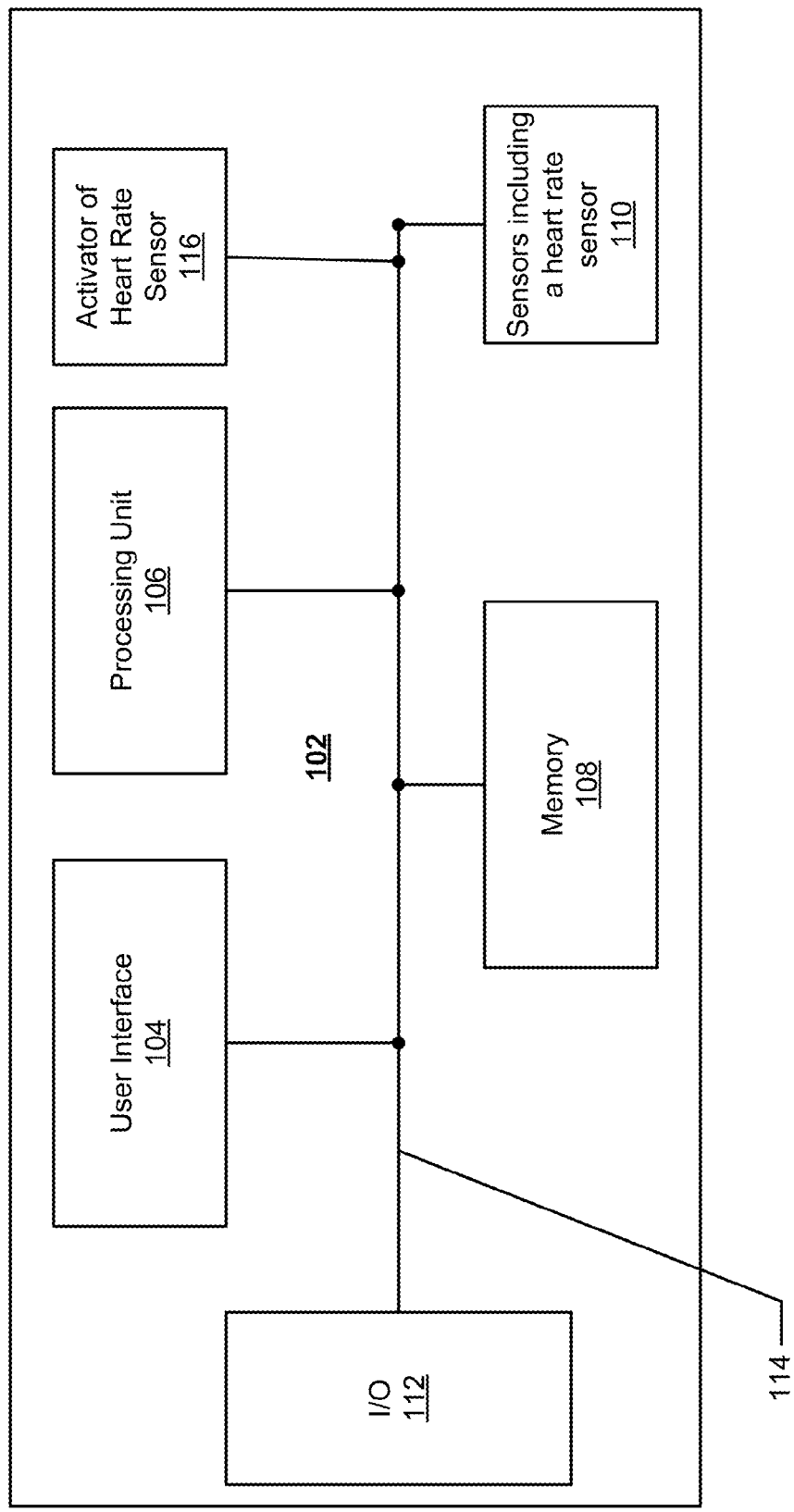
FIG. 1 depicts a generalized schematic of an example computing device that may be used to implement a portable biometric monitoring device or other device with which the heart rate monitoring and various other operations described herein may be executed.

FIG. 1 depicts a generalized schematic of an example portable biometric monitoring device, also simply referred to herein as "biometric monitoring device," or other device with which the various operations described herein may be executed. The portable biometric monitoring device 102 may include a processing unit 106 having one or more processors, a memory 108, a user interface 104, one or more biometric sensors 110, and input/output 112. The processing unit 106, the memory 108, the user interface 104, the one or more biometric sensors 110, and the input/output interface 112 may be communicatively connected via communications path(s) 114. It is to be understood that some of these components may also be connected with one another indirectly. In some embodiments, components of FIG. 1 may be implemented as an external component communicatively linked to other internal components. For instance, in one embodiment, the memory 108 may be implemented as a memory on a secondary device such as a computer or smart phone that communicates with the device wirelessly or through wired connection via the I/O interface 112. In another embodiment, the User Interface may include some components on the device such as a button, as well as components on a secondary device communicatively linked to the device via the I/O interface 112, such as a touch screen on a smart phone.

The portable biometric monitoring device may collect one or more types of biometric data, e.g., data pertaining to physical characteristics of the human body (such as heartbeat, perspiration levels, etc.) and/or data relating to the physical interaction of that body with the environment (such as accelerometer readings, gyroscope readings, etc.), from the one or more sensors 110 and/or external devices (such as an external blood pressure monitor). In some embodiments, the one or more sensors 110 include a heart rate sensor that is configured to be activated by an activator 116 of the heart rate sensor. In some embodiments, the activator 116 is also a biometric sensor, such as an accelerometer serving as both an activator of the heart rate sensor and as a motion sensor. In other embodiments, the activator may be a single-purpose device, e.g., a touch sensor or button. The activator, in general, is a mechanism through which a user input or activation signal may be received or recognized by the device in order to initiate heart rate measurement via the heart rate sensor. In some embodiments, the device stores collected information in memory 108 for later use, e.g., for communication to another device via the I/O interface 112, e.g., a smartphone or to a server over a wide-area network such as the Internet.

Biometric information, as used herein, refers to information relating to the measurement and analysis of physical or behavioral characteristics of human or animal subjects. Some biometric information describes the relation between the subject and the external environment, such as altitude or course of a subject. Other biometric information describes the subject's physical condition without regard to the external environment, such as the subject's heart rate. The information concerning the subject is generally referred to as biometric information. Similarly, sensors for collecting the biometric information are referred to herein as biometric sensors. In contrast, information about the external environment regardless of the subject's condition is referred to as environmental information, and sensors for collecting such information are referred to herein as environmental sensors. It is worth noting that sometimes the same sensor may be used to obtain both biometric information and environmental information. For instance, a light sensor worn by the user may function as part of a photoplethysmography (PPG) sensor that gathers biometric information based on the reflection of light from the subject (such light may originate from a light source in the device that is configured to illuminate the portion of the person that reflects the light). The same light sensor may also gather information regarding ambient light when the device is not illuminating the portion of the person. In this disclosure, the distinctions between biometric and non-biometric information and sensors are drawn for organizational purposes only. This distinction is not essential to the disclosure, unless specified otherwise.

The processing unit 106 may also perform an analysis on the stored data and may initiate various actions depending on the analysis. For example, the processing unit 106 may determine that the data stored in the memory 108 indicates that a goal threshold has been reached and may then display content on a display of the portable BMD celebrating the achievement of the goal. The display may be part of the user interface 104 (as may be a button or other control, not pictured, that may be used to control a functional aspect of the portable biometric monitoring device). In some embodiments, the user interface 104 includes components in or on the device. In some embodiments, the user interface 104 also includes components external from the device that are nonetheless communicatively linked to the device. For instance, a smartphone or a computer communicatively linked to the BMD may provide user interface components through which a user can interact with the BMD.

In general, BMDs may incorporate one or more types of user interfaces including but not limited to visual, auditory, touch/vibration, or combinations thereof. The BMD may, for example, display information relating to one or more of the data types available and/or being tracked by the biometric monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the biometric monitoring device. For example, moving the BMD in a "figure 8" motion or double tapping the BMD may be recognized by the biometric monitoring device as a user input that will cause the display of the biometric monitoring device to turn on from an off state or that will cause the biometric monitoring device to transition between different monitoring states, e.g., transitioning a heart rate sensor from an "off" to an "on" state.

In one example, while the user is wearing the biometric monitoring device 102, the biometric monitoring device 102 may measure and store a user's heart rate while the user is wearing the biometric monitoring device 102 and then subsequently transmit data representative of heart rate to the user's account on a web service like fitbit dot com, to a mobile computational device, e.g., a phone, paired with the portable biometric monitoring unit, and/or to a standalone computer where the data may be stored, processed, and visualized by the user. Such data transmission may be carried out via communications through I/O interface 112. The device can also derive and/or provide information related to heart rate, such as average heart rate, minimum heart rate, maximum heart rate, heart rate variability, heart rate relative to target heart rate zone, heart rate relative to resting heart rate, change in heart rate, heart rate recovery, training advice with reference to heart rate, a medical condition with reference to heart rate. In addition, the device may measure, calculate, or use a plurality of other physiological metrics other than the user's heart rate. These include, but are not limited to, step count, caloric energy expenditure, floors climbed or descended, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the biometric monitoring device from an external source, e.g., the user may input their height, weight, and stride in a user profile on a fitness-tracking website and such information may then be communicated to the biometric monitoring device via the I/O interface 112 and used to evaluate, in tandem with data measured by the sensors 110, the distance traveled or calories burned by the user. The device may also measure or calculate metrics related to the environment around the user such as barometric pressure, weather conditions, light exposure, noise exposure, and magnetic field.

As mentioned previously, collected biometric data from the biometric monitoring device may be communicated to external devices through the communications or I/O interface 112. The I/O or communications interface may include wireless communication functionality so that when the biometric monitoring device comes within range of a wireless base station or access point, the stored data automatically uploads to an Internet-viewable source such as a website, e.g., fitbit dot com. The wireless communications functionality may be provided using one or more communications technologies known in the art, e.g., Bluetooth, RFID, Near-Field Communications (NFC), Zigbee, Ant, optical data transmission, etc. The biometric monitoring device may also contain wired communication capability, e.g., USB.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 1 illustrates a generalized implementation of a biometric monitoring device 102 that may be used to implement a portable biometric monitoring device or other device in which the various operations described herein may be executed. It is to be understood that in some implementations, the functionality represented in FIG. 1 may be provided in a distributed manner between, for example, an external sensor device and communication device, e.g., an external blood pressure meter that may communicate with a biometric monitoring device.

Moreover, it is to be understood that in addition to storing program code for execution by the processing unit to effect the various methods and techniques of the implementations described herein, the memory 108 may also store configuration data or other information used during the execution of various programs or instruction sets or used to configure the biometric monitoring device. The memory 108 may also store biometric data collected by the biometric monitoring device. In some embodiments, the memory may be distributed on more than one devices, e.g., spanning both the BMD and an external computer connected through the I/O 112. In some embodiments, the memory may be exclusively located on an external device. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

It is to be further understood that the processing unit 106 may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit.

Though not shown, numerous other functional blocks may be provided as part of the biometric monitoring device 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the biometric monitoring device 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. The various methods and techniques disclosed herein may be implemented through execution of one or more a sequences of instructions, e.g., software programs, by the processing unit 106 or by a custom-built hardware ASIC (application-specific integrated circuit) or programmed into a programmable hardware device such as an FPGA (field-programmable gate array), or any combination thereof within or external to the processing unit 106.

Further implementations of portable biometric monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the biometric monitoring device may include computer-executable instructions for controlling one or more processors of the biometric monitoring device to obtain biometric data from one or more biometric sensors. The instructions may also control the one or more processors to receive a request, e.g., an input from a button or touch interface on the biometric monitoring device, a particular pattern of biometric sensor data (e.g., a double-tap reading), etc., to display an aspect of the obtained biometric data on a display of the biometric monitoring device. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data. The instructions may also cause the display to turn off from an on state after a predefined time period elapses without any user interaction with the biometric monitoring device; this may assist in conserving power.

Due to the small size of many biometric monitoring devices, many biometric monitoring devices may have limited space to accommodate various user interface components. For example, Fitbit makes a variety of extremely compact biometric tracking units that each incorporates a biometric sensor suite, a battery, a display of some sort, a charging interface, and one or more wireless communications interfaces. In some such examples, the biometric tracking units also incorporate a vibramotor and/or a button. These components may be housed, for example, within housings measuring approximately 2" long, 0.75" wide, and 0.5" thick (Fitbit ULTRA™); approximately 1.9" in length, 0.75" wide, and 0.375" thick (Fitbit ONE™); approximately 1.4" long, 1.1" wide, and 0.375" thick (Fitbit ZIP™); and approximately 1.3" in length, 0.5" wide, and 0.25" thick (Fitbit FLEX™). Of course, housings of other sizes may be used in other implementations of biometric monitoring devices; the above list is merely intended to illustrate the small size of many such biometric monitoring devices.

Despite the small sizes of the above-listed Fitbit devices, each includes a display of some type—the Fitbit ULTRA™, Fitbit ONE™, and Fitbit ZIP™, for example, all include small pixelated display screens capable of outputting text, numbers, and graphics. The Fitbit FLEX™, due to its smaller size, uses discrete light-emitting diode (LED) indicators, e.g., 5 LEDs arranged in a row, to convey information visually. Each of the above-listed Fitbit devices also has an input mechanism that allows a user to affect some aspect of the device's operation. For example, the Fitbit ULTRA™ and Fitbit ONE™ each include a discrete pushbutton that allows a user to affect how the device operates. The Fitbit ZIP™ and Fitbit FLEX™, by contrast, do not have a discrete pushbutton but are instead each configured to detect, using their biometric sensors, when the user taps the housing of the device; such events are construed by the processor or processors of such devices as signaling a user input, i.e., acting as the input mechanism. In some implementations of biometric monitoring devices described herein, the biometric monitoring devices may have only one mechanism, e.g., biometric sensors, for receiving input from a wearer (other than wireless or wired links to other devices). In some other implementations, the biometric monitoring device may include only one mechanism, e.g., a touch sensitive area, other than the biometric sensors in the biometric monitoring device for receiving input from a wearer. For instance, in some embodiments, the biometric monitoring device includes a heart rate sensor and a touch sensitive area. The touch sensitive area functions as an activator for the heart rate sensor, such that when a user touches the area, an activation signal is detected, which triggers the heart rate sensor to collect heart rate related data from the user. In some embodiments, the heart rate related data is collected through the same touch sensitive area, such that a single touch-and-hold user gesture triggers the data collection and allows data to be collected from the body part that triggers the data collection.

In some implementations, one or more components of 102 may be distributed across multiple devices, forming a biometric monitoring system 102 spanning multiple devices. Such implementations are also considered to be within the scope of this disclosure. For instance, the user interface 104 on a first device may not have any mechanism for receiving physical input from a wearer, but the user interface 104 may include a component on a second, paired device, e.g., a smart phone, that communicates wirelessly with the first device. The user interface 104 on the smart phone allows a user to provide input to the first device, such as providing user names and current location. Similarly, in some implementations, a biometric monitoring device may not have any display at all, i.e., be unable to display any biometric data directly—biometric data from such biometric monitoring devices may instead be communicated to a paired electronic device, e.g., a smartphone, wirelessly and such biometric data may then be displayed on data display screens shown on the paired electronic device. Such implementations are also considered to be within the scope of this disclosure, i.e., such a paired electronic device may act as a component of the biometric monitoring system 102 configured to communicate with biometric sensors located internal or external to the paired electronic device (such biometric sensors may be located in a separate module worn elsewhere on the wearer's body).

Single-Gesture Heart Rate Monitoring

In some embodiments, the biometric monitoring device provides a heart rate monitoring function requiring only a single user-gesture in order to collect heart rate data. In some embodiments, the heart rate monitoring function initiates heart rate data collection in response to a single user-gesture. In some embodiments, the device provides user feedback regarding the collected heart rate data without requiring further user input. The present inventors have realized that heart rate monitoring activated by a single user-gesture is desirable. As used herein, a "single user-gesture" is an action of a user relative to a single part of the apparatus, wherein the action is interpreted by the apparatus as a single behavioral pattern. Examples of a single user-gesture includes, but are not limited to, a single touch of a surface of an apparatus, touching and holding a button, a double tap on the same part of a device that is interpreted as a single behavioral pattern indicating a single command, shaking of the device, moving the device in a certain trajectory, e.g., a "figure 8" trajectory, staring at the apparatus or a particular portion of the apparatus (when the apparatus has gaze detection function), bringing a body part into proximity with the apparatus, bringing an arm wearing a wristband-type BMD from a downwards-extended position to a viewing position, twisting the wrist wearing a BMD implemented as wrist band, etc. One example that is not a single user-gesture is touching a button of a device twice wherein each touch is interpreted by the device as a separate behavioral pattern, each pattern indicating a command, e.g., a command to activate a function or advance a display from one screen of information to a next. Another example of an action that is not a single user-gesture is touching two different parts of a device, for example, touching a button with one body part while touching a sensor component with another body part (or touching two separate sensor components with two different body parts). Yet another example of an action that is not a single user-gesture or interaction is to scroll through a touch screen and then tap an icon or contact the device to activate data collection. It is also to be understood that the mere act of normally wearing a BMD is not a "user-gesture" as used herein, e.g., strapping or wearing a wristband BMD onto one's wrist is not a user-gesture as used herein.

The single user-gesture may cause the biometric monitoring device to obtain a heart rate measurement regardless, or largely regardless, of what mode the biometric monitoring device is in at the time the single user-gesture is detected by the biometric monitoring device. For example, the biometric monitoring device may be in a state where the display is off, and the biometric monitoring device may receive the single user-gesture and take a heart rate measurement. In another example, the biometric monitoring device may be in a state where the display is displaying a biometric performance measurement, e.g., steps taken or distance traveled, and the biometric monitoring device may receive the single user-gesture and take a heart rate measurement without requiring the that user first change screens or otherwise interact with the biometric monitoring device (aside from providing the single user-gesture). Generally speaking, during normal operation of the biometric monitoring device, receipt of a single user-gesture may, without requiring any further or preparatory interaction of the user with the biometric monitoring device, cause the biometric monitoring device to obtain a heart rate measurement, as discussed herein.

Figure 2A:
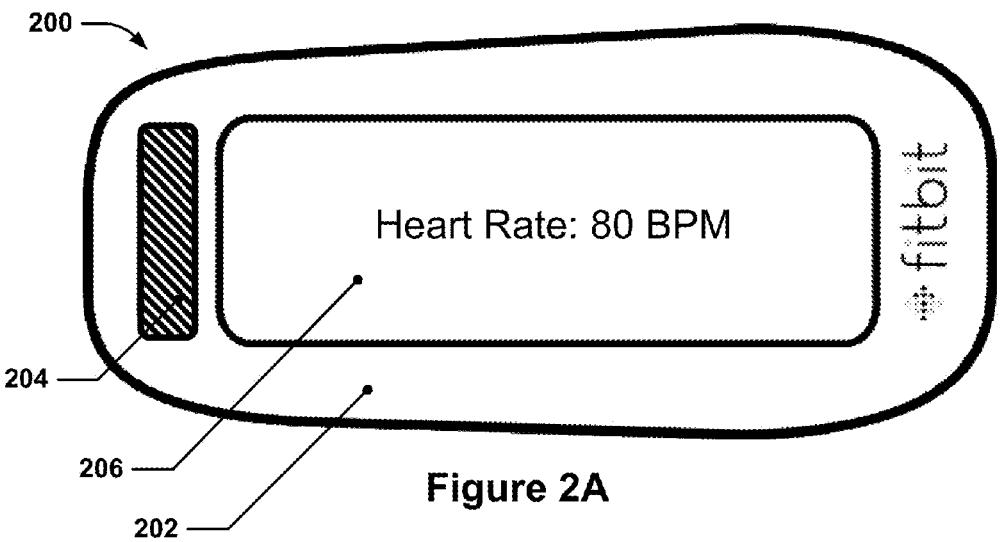
FIGS. 2A and 2B depict two examples of biometric monitoring devices with heart rate monitoring function and having a button and a display.
Figure 2B:
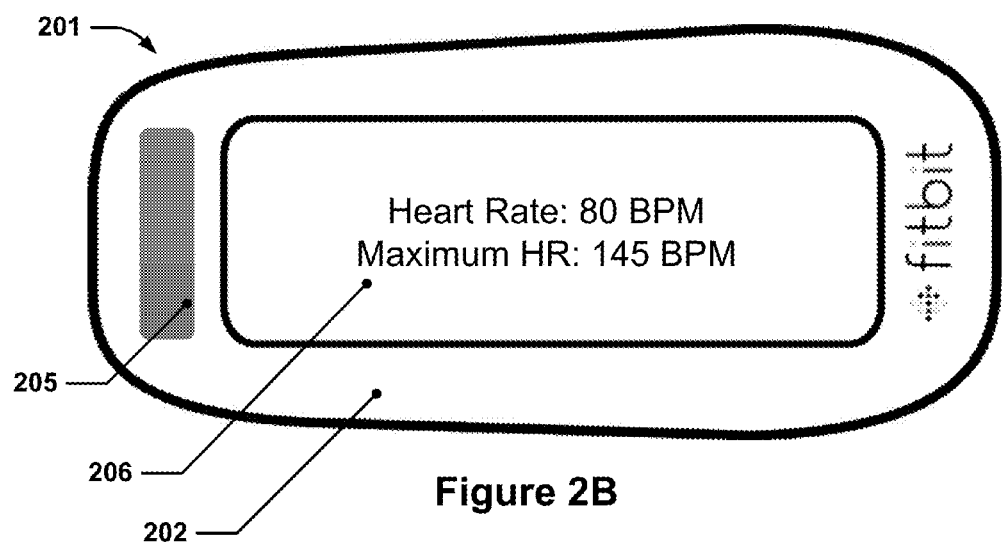

As mentioned above, various implementations of portable biometric monitoring devices described herein may have shapes and sizes adapted for coupling to the body or clothing of a user (e.g., secured to, worn, borne by, etc.). Various examples of such portable biometric monitoring devices are shown in FIGS. 2-5. FIGS. 2A-2B depict two biometric monitoring devices 200 and 201 similar in shape to a Fitbit ONE™, which may be inserted into a holder with a belt clip or into a pocket on a wristband. As used herein, the term "wristband" may refer to a band that is designed to fully or partially encircle a person's forearm near the wrist joint. The band may be continuous, e.g., without any breaks (it may stretch to fit over a person's hand or have an expanding portion similar to a dress watchband), or may be discontinuous, e.g., having a clasp or other connection allowing the band to be closed similar to a watchband or may be simply open, e.g., having a C-shape that clasps the wearer's wrist.

Biometric monitoring device 200 in FIG. 2A includes a housing 202 that contains the electronics associated with the biometric monitoring devices 200. Among other sensors, the housing 202 includes a heart rate sensor and an activator of the heart rate sensor. The heart rate sensor is an optical sensor such as the optical sensor assembly 500 shown in FIG. 5. The optical sensor may be configured as a photoplethysmography (PPG) sensor or pulse oximetry sensor. The activator can be a pressure or touch sensitive sensor, e.g., capacitive touch, resistive touch, ultrasonic touch, etc., or a proximity sensor, e.g., infrared, capacitive, etc., as described in the sensor section of the disclosure. Notably, the heart rate sensor collects data through a heart rate sensor surface area located in the area of button 204. Therefore, the button has a surface that is optically transparent for the optical sensor, e.g., infrared transparent for an infrared sensor. Furthermore, the activator receives input through an activator surface area, which also is located in the area of button 204. The collocation of the sensor surface area and the activator surface area allows the same body part that touches button 204 to provide activation signal to the activator and heart rate related blood volume signal to the optical sensor. This is design allows a single user-gesture of pressing the button 204 to send an activation signal to the activator, which causes the heart rate sensor to collect heart rate data from the same body part that presses the button 204, eliminating the complication of using multiple user gestures to activate the heart rate sensor and to provide physiological data to the sensor. Biometric monitoring device 200 also includes a display 206 that may be accessible/visible through the housing 202. In some embodiments, the display automatically shows measured heart rate related information without requiring further user input. This further simplifies the user experience to get a heart rate reading. Biometric monitoring devices 200 and 201 are similar except that device 200 has a button 204 for user input, while device 201 has a touch sensitive surface 205 that merges seamlessly with the device housing 202. The touch sensitive surface 205 provides a signal path for an activator, such as an IR-based proximity detector or a capacitive touch/proximity detector.

When the heart rate sensor that is used in such embodiments is a PPG sensor (or other single-point-of-measurement heart rate sensor), then such embodiments may not only initiate heart rate collection responsive to a single user-gesture, but they may also allow for the collection of heart rate data without any further interaction of the user with the device. This is because a PPG sensor may detect heart rate through taking measurements from a single body part, e.g., a wrist or a finger. In contrast, an electrocardiograph (EKG) heart rate sensor requires that measurements be taken from multiple electrodes, each in contact with a different part of the body. Thus, a PPG-based embodiment may be particularly well-suited to measuring data from a single user-gesture and a single body part. While an EKG-based embodiment may be able to initiate a measurement based on a single gesture, it requires contact of multiple body parts (usually on opposite sides of the heart from one another) with the EKG sensor electrodes in order to function. Thus, if a user wished to take a heart rate measurement while the device is in their pocket, they would easily be able to do so with a PPG-based, single gesture heart rate measurement device, but would find it very difficult or impossible to do so with an EKG-based, single gesture heart rate measurement device since they would be unable to fit two both hands in their pocket (and would look ungainly in trying to do so).

In some embodiments, the heart rate sensor surface area and the activator surface area are less than 2, or less than 1, or less than 0.5 centimeters apart as measured by the distance along the exterior surface of the housing, thereby allowing a single body part of a user to simultaneously interact with the activator and the heart rate sensor. In some embodiments, the heart rate sensor surface area and the activator surface area overlap as measured by the distance along the exterior surface of the housing. In some embodiments, the heart rate sensor surface area seamlessly joins the surface of the housing. In some embodiments, the activator surface area seamlessly joins the surface of the housing. In some embodiments, the apparatus has only one heart rate sensor surface area. In other embodiments, the apparatus has two or more heart rate sensor surface areas and two or more heart rate sensors.

In some embodiments, the heart rate sensor surface area and the activator surface area are arranged on a substantially flat plane or a nominally common surface, thereby allowing a single body part of a user to simultaneously interact with the activator and the heart rate sensor. Many BMDs feature "organic" shapes, e.g., smoothly rounded or blended exterior surfaces, which may make it difficult to define where one surface begins and another ends. Thus, it may be more useful to describe a nominally common surface in the negative—for example, surfaces that, for the most part, face in completely opposite directions (e.g., a front surface and a back surface) are not, for the purposes of this disclosure, considered to be a nominally common surface. The term "substantially flat plane" may refer to both a true flat plane as well as a smoothly-curved surface that is largely free of drastic curvature (the display and button area of a Fitbit One™ BMD provides one example of a "substantially flat plane."

Figure 3:
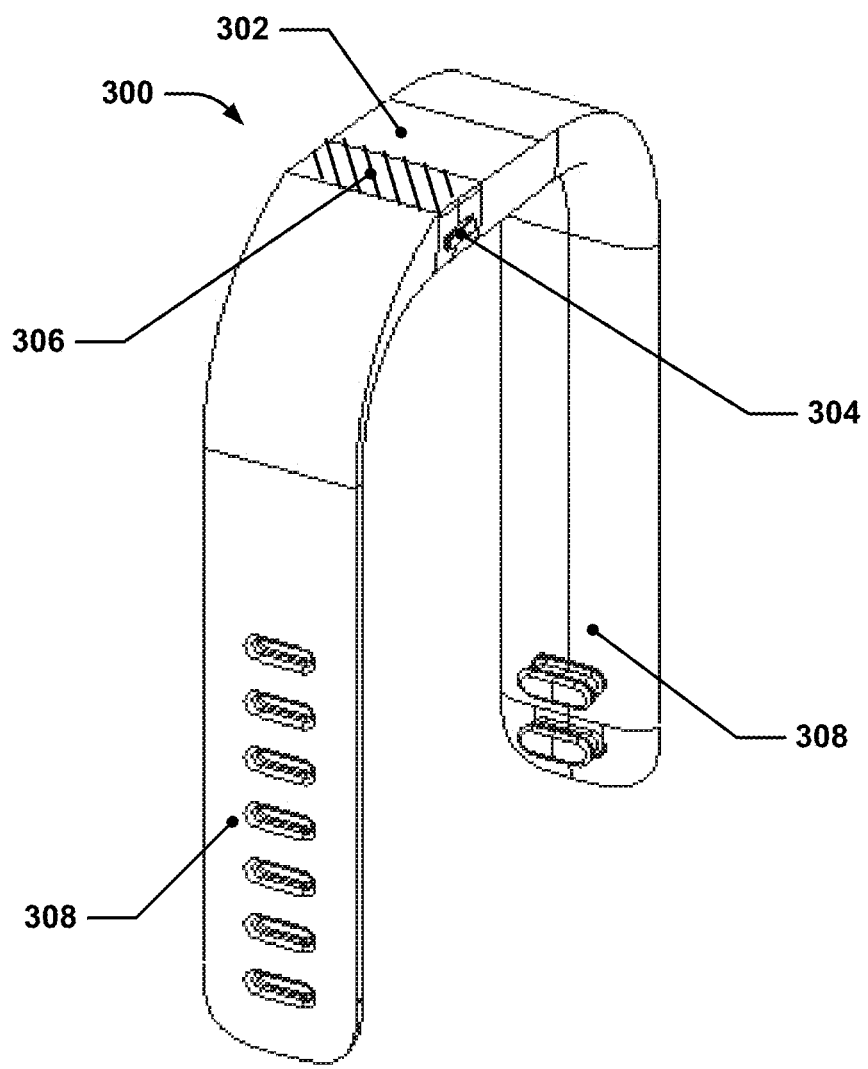
FIG. 3 depicts an example of a wrist-mounted biometric monitoring device with heart rate monitoring function having a button, a display, and a band to secure the biometric monitoring device to a user's forearm.

FIG. 3 depicts a biometric monitoring device that may be worn on a person's forearm like a wristwatch, much like a Fitbit FLEX™ or FORCE™. Biometric monitoring device 300 has a housing 302 that contains the electronics associated with the biometric monitoring device 300. A button 304 and a display 306 may be accessible/visible through the housing 302. A wristband 308 may be integrated with the housing 302. In some embodiments, the button 304 may be implemented similarly as the button 204 of FIG. 2A, which provides a mechanism to activate a heart rate sensor to collect heart rate data in response to a single user-gesture. In some embodiments, the display 306 may be implemented similarly as the touch sensitive surface 205 of FIG. 2B, providing a mechanism to activate a heart rate sensor to collect heart rate data in response to a single user-gesture.

Figure 4:
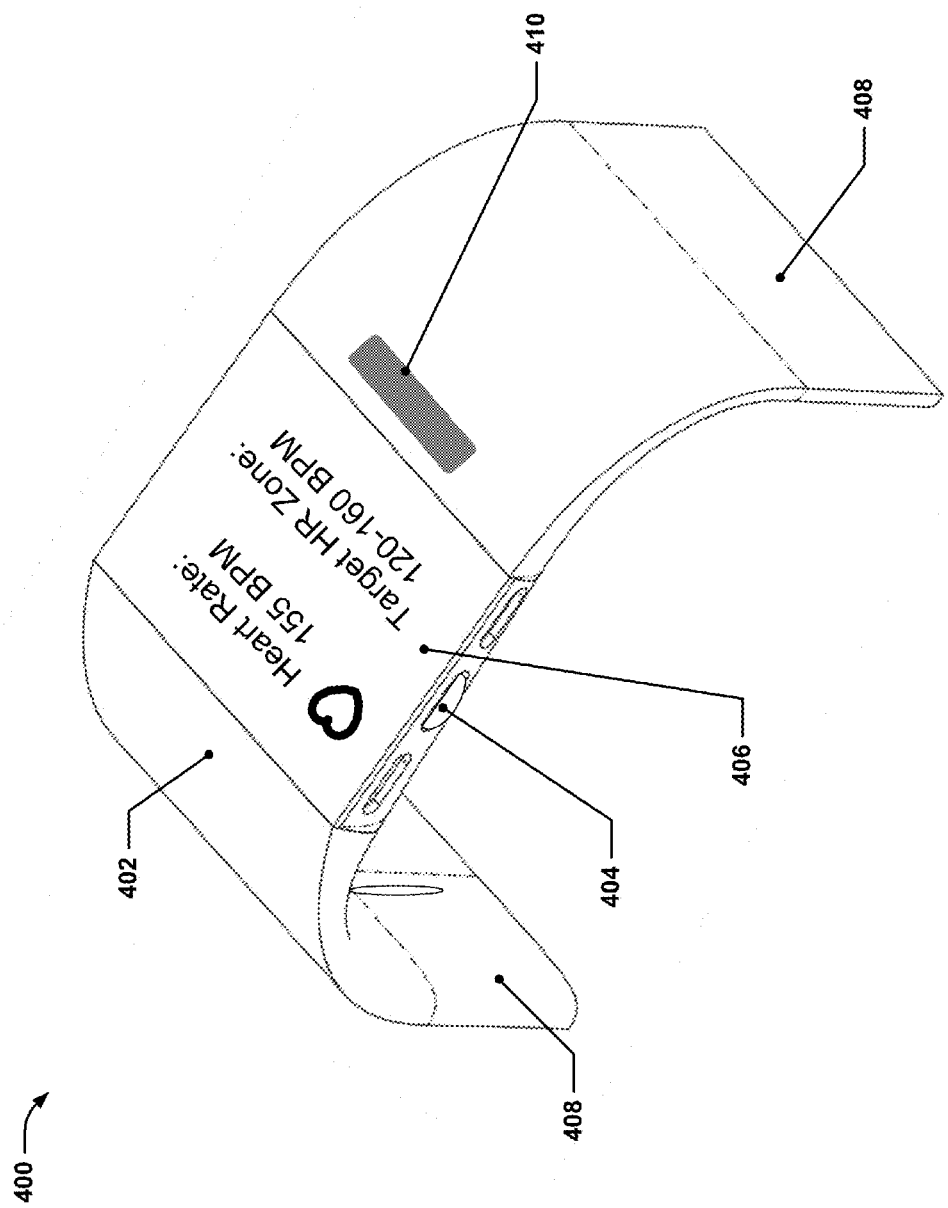
FIG. 4 depicts another example of a wrist-mounted biometric monitoring device with heart rate monitoring function having a button, a display, a touch sensitive area, and a band to secure the biometric monitoring device to a user's forearm.

FIG. 4 depicts another example of a biometric monitoring device that may be worn on a person's forearm like a wristwatch, although with a bigger display than the biometric monitoring device of FIG. 3. Biometric monitoring device 400 has a housing 402 that contains the electronics associated with the biometric monitoring device 400. A button 404 and a display 406 may be accessible/visible through the housing 402. A wristband 408 may be integrated with the housing 402, which includes a touch sensitive area 410 similar to the touch sensitive area 205 described above, providing a mechanism to activate a heart rate sensor to collect heart rate data in response to a single user-gesture. In some embodiments, the button 404 may be implemented in the same manner as the button of 204, providing a mechanism to activate a heart rate sensor to collect heart rate data in response to a single user-gesture.

Figure 5:
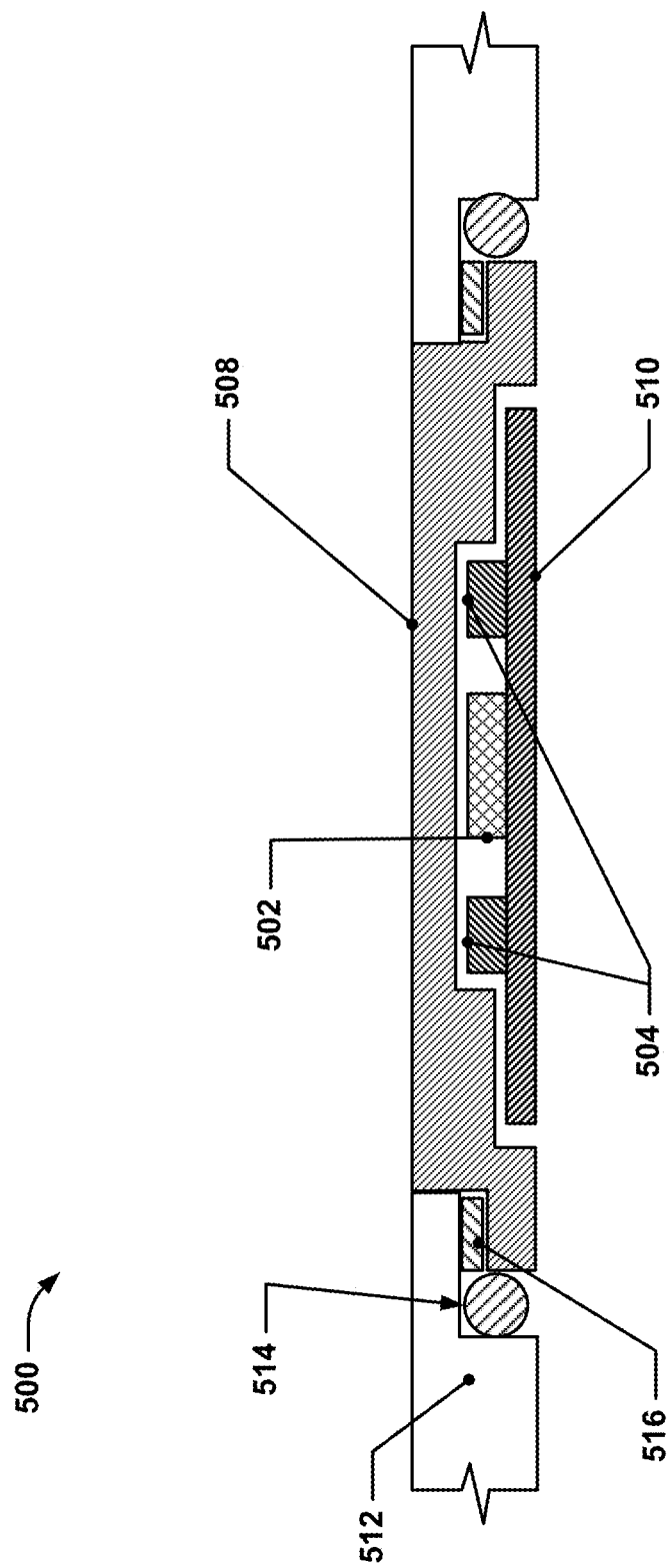
FIG. 5 provides another cross-sectional view of a PPG sensor. Of note in this PPG sensor is the lack of a protrusion. Additionally, a liquid gasket and/or a pressure sensitive adhesive are used to prevent liquid from entering the device body.

In some embodiments such as those shown in FIGS. 2 to 4, the biometric monitoring devices include an optical sensor under a flat optical sensor area. FIG. 5 shows one implementation of such an optical sensor. The optical sensor includes two LEDs 504 as light sources. The optical sensor also includes a photodetector 502. An optically transparent layer covers the LEDs 504 in the photo detector 502, providing protection to the elements. The optically transparent layer 508 serves as the sensor surface area through which the photodetector collects heart rate data. Furthermore, the optically transparent layer also serves as the activator surface area, through which an activation signal indicating a single user gesture can be detected by activator. In some embodiments, the photodetector 502 can function as an activator by detecting ambient light, wherein an ambient light drop indicates the user has covered the activator surface area. Upon such signal, the LEDs 504 are activated to emit light, and the photodetector collects reflection from the user's skin and tissue indicating heart rate information. In other embodiments, a separate sensor is implemented as the activator, such as an infrared proximity sensor or a capacitive touch sensor (not shown).

In addition to the optical sensor elements, the biometric monitoring device also includes a printed circuit board (PCB) 510, atop which the photodetector 502 and the LEDs 504 reside. In some embodiments, the optically transparent layer 508 is secured to the device body 512 by pressure sensitive adhesives 516 and liquid gaskets 514. In other embodiments, the optically transparent layer is seamlessly merged with the top layer of the device body (not shown). This latter embodiment provides a more aesthetic appearance and a better seal, but it will not allow the optically transparent layer 508 to depress relative to the device body.

Figure 6:
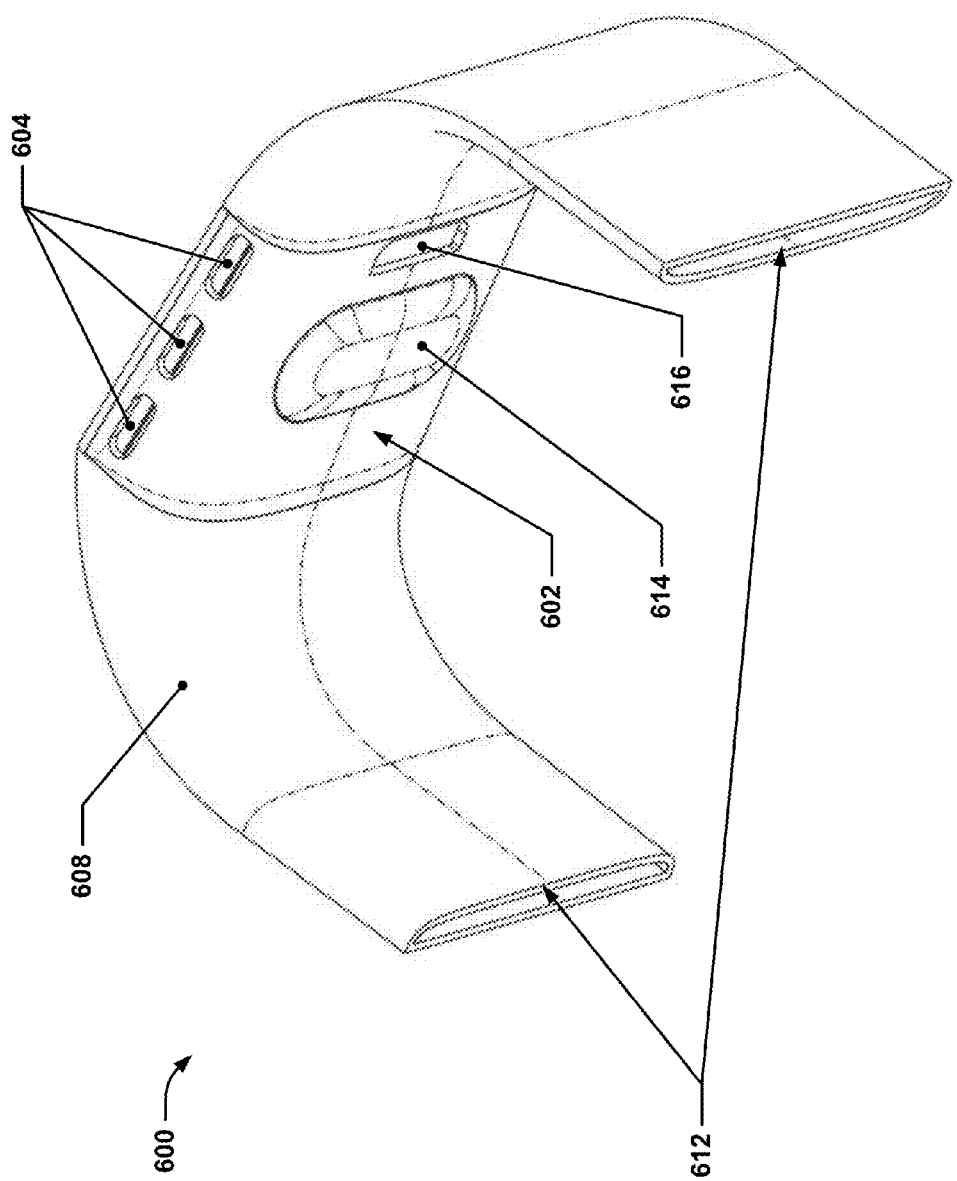
FIG. 6 provides a view of a portable monitoring device which shows the skin-facing portion of the device. On this side, a sensor protrusion and recess for mating a charger and/or data transmission cable can be seen.

The biometric monitoring device is adapted to be worn or carried on the body of a user. In some embodiments including the optical heart rate monitor, the device may be a wrist-worn or arm-mounted accessory such as a watch or bracelet. In one embodiment, optical elements of the optical heart rate sensor are located on the interior or skin side of the biometric monitoring device, for example, in a sensor protrusion 614 facing and adjacent to the top of the wrist when the device 600 of FIG. 6 is wrist mounted. Biometric monitoring device 600 also includes a device housing 602, buttons 604 that are similar to button 204 of FIG. 4, which is implemented as a mechanism for collecting data in response to a single user-gesture. Furthermore, biometric monitoring device 600 also includes securing method 612 such as a hook and loop or clasp. The device also includes an attachment band 608 and a charger mating recess 616.

In some embodiments, the optical heart rate monitor is located on one or more external surfaces of the biometric monitoring device that do not substantially contact the wearer's body when worn, such as the one or more buttons 604 of device 600. In this embodiment, the user may touch an optical window on a button 604 (behind which optical elements of the optical heart rate monitor are located) with a finger on the opposing hand to initiate a heart rate measurement (and/or other metrics related to heart rate such as heart rate variability) and/or collect data which may be used to determine the user's heart rate (and/or other metrics related to heart rate) In some embodiments, a biometric monitoring device need not be worn on the wrist in order to engage the heart rate measurement since the heart rate may be obtained through the single user-interaction with the button). In one embodiment, the biometric monitoring device 600 may trigger or initiate the measurement(s) by detecting a (sudden) drop in incident light on the photodiode—for example, when the user's finger is placed over the optical window. In this embodiment, the incident light sensor functions as the activator of the heart rate sensor. In addition thereto, or in lieu thereof, a heart rate measurement (or other such metric) may be trigged by an IR-based proximity detector and/or capacitive touch/proximity detector (which may be separate from other detectors) functioning as activator of the heart rate sensor. Such IR-based proximity detector and/or capacitive touch/proximity detector may be disposed in or on and/or functionally, electrically and/or physically coupled to the optical window to detect or determine the presence of a single user-gesture, such as a finger touching or in proximity of the buttons 604.

In one embodiment, the biometric monitoring device may include a button which, when depressed, triggers or initiates heart rate measurement (and/or other metrics related to heart rate). The button may be disposed in close proximity of the optical window to facilitate the user pressing the button while the finger is disposed on the optical window. In one embodiment, the optical window may be embedded in a push button. Thus, when the user presses the button, it could trigger a measurement via the user's finger which depresses the button. Indeed, the button may be given a shape and/or resistance to pressing that enhances or optimizes a pressure profile against the finger to provide high SNR during measurement or data acquisition. In other embodiments (not illustrated), the biometric monitoring device may take the form of a clip, smooth object, pendant, anklet, belt, etc. that is adapted to be worn on the body, clipped or mounted to an article of clothing, deposited in clothing (e.g., pocket), or deposited in an accessory (e.g., handbag).

In one specific embodiment, the biometric monitoring device includes a protrusion 614 on the skin- or interior-side of the device. When contacting the user, the protrusion 614 engages the skin with more force than the surrounding device body. In this embodiment, an optical window or light transmissive structure may form or be incorporated in a portion of the protrusion. The light emitter(s) and/or detector(s) of the optical sensor may be disposed or arranged in the protrusion juxtaposed the window or light transmissive structure. As such, when attached to the user's body, the window portion of the protrusion of the biometric monitoring device engages the user's skin with more force than the surrounding device body—thereby providing a more secure physical connection between the user's skin and the optical window. That is, a protrusion improves sustained contact between the biometric monitoring device and the user's skin which may reduce the amount of stray light measured by the photodetector, decrease motion between the biometric monitoring device and the user, and/or provide improved local pressure to the user's skin; all of which may increase the quality of the cardiac signal of interest. Notably, the protrusion may contain other sensors that benefit from close proximity and/or secure contact to the user's skin. These may be included in addition to or in lieu of a heart rate sensor and include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

Figure 7:
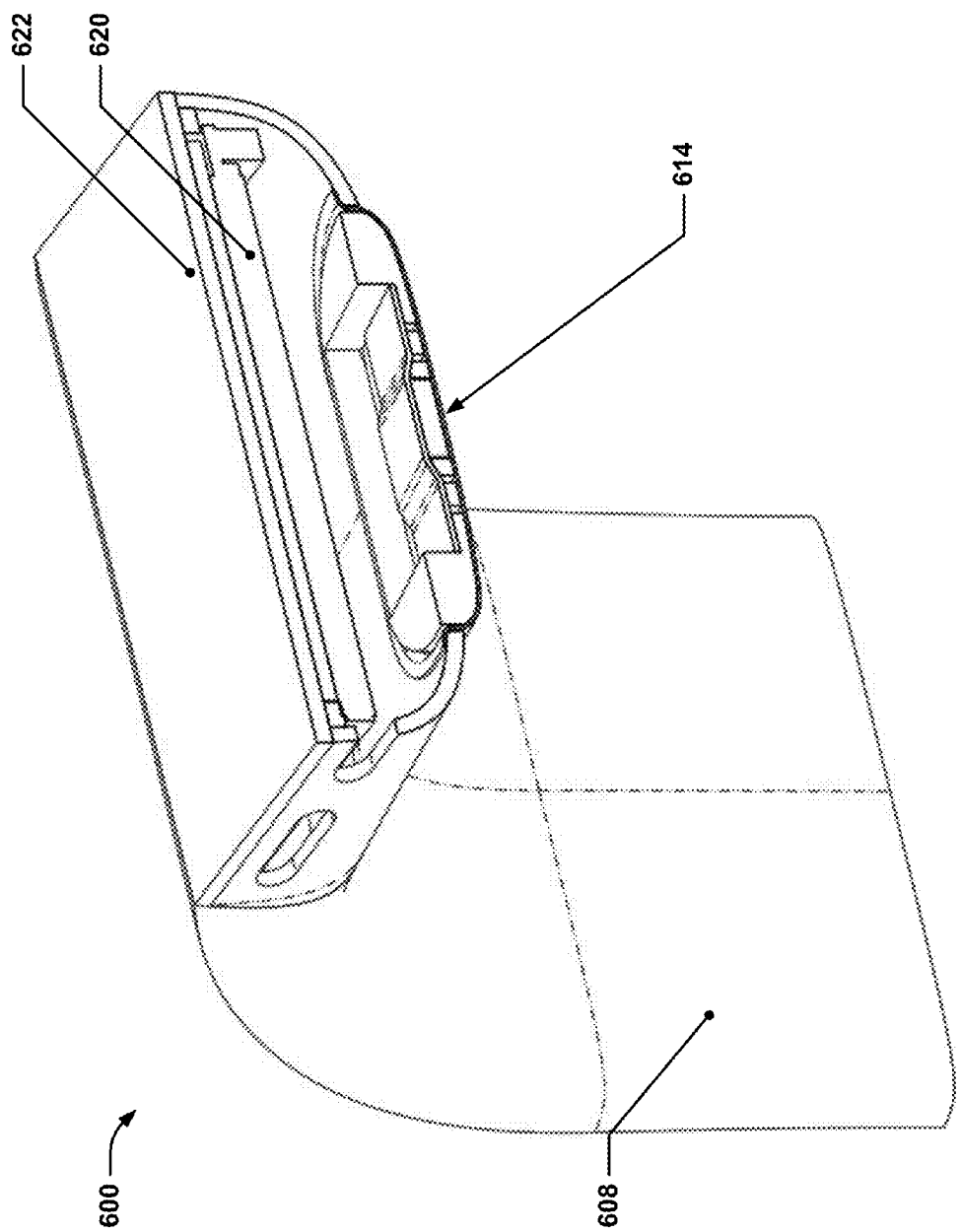
FIG. 7 provides a cross-sectional view of a portable monitoring device. This cross-section is through the electronics package. Of note are the sensor protrusion, main PCB board and display.
Figure 8:
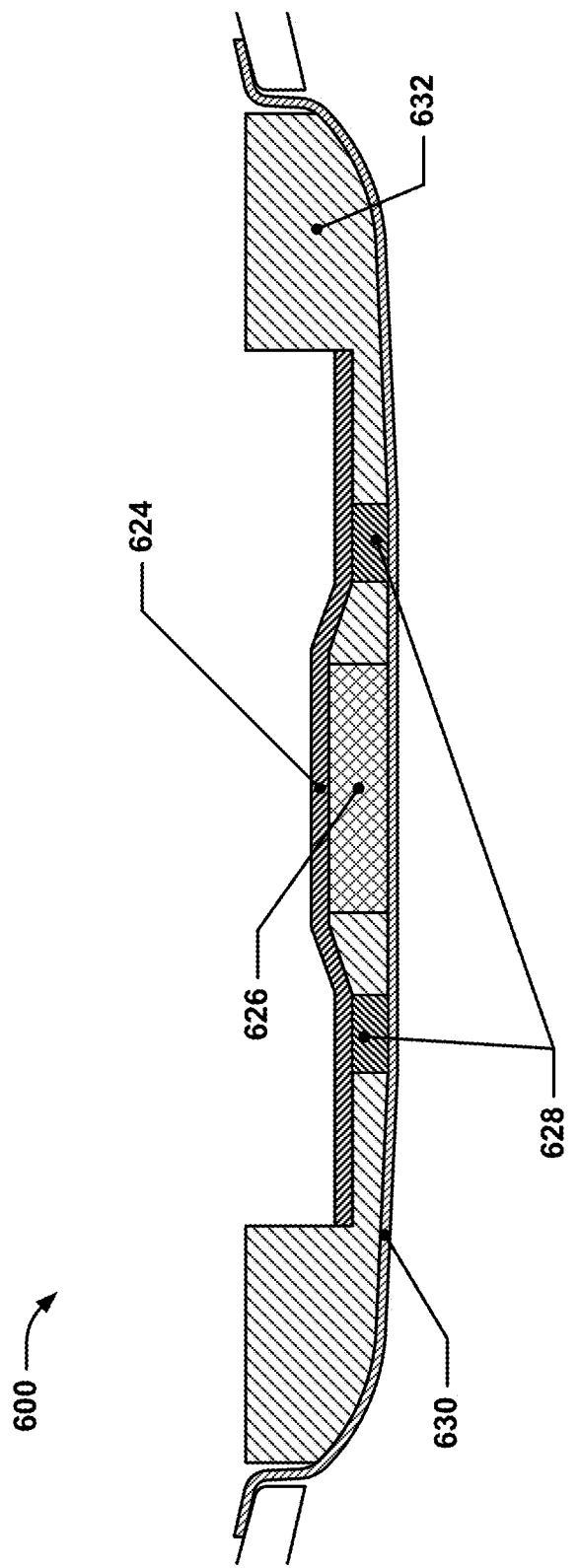
FIG. 8 provides a cross sectional view of a sensor protrusion of a portable monitoring device. Two light sources (e.g. LED's) are placed on either side of a photodetector to enable PPG sensing. A light-blocking material is placed between the light sources and the photodetector to prevent any light from the light sources from going through the device body and being detected by the photodetector. A flexible transparent layer may be placed on the lower surface of the sensor protrusion to form a seal. This transparent layer may serve other functions such as preventing liquid from entering the device where the light sources or photodetectors are placed. This transparent layer may be formed through in-mold labeling or "IML". The light sources and photodetector are placed on a flexible PCB.

FIG. 7 shows a cross-sectional view of biometric monitoring device 600, revealing the interior of the protrusion 614, a printed circuit board (PCB) 620, and a display 622. Figure 8 shows further details of elements of the optical sensor of biometric monitoring device of 600. The optical sensor includes a photodetector 626, and two LEDs 628 as light sources. It also includes protective transparent layer 630 covering and protecting the photodetectors 626 and the LEDs 628. Light blocking material 632 fills the space around the LEDs 628 and the photodetector 626. The flexible PCB 624 sits atop LEDs 628 and photodetector 626.

Figure 9:
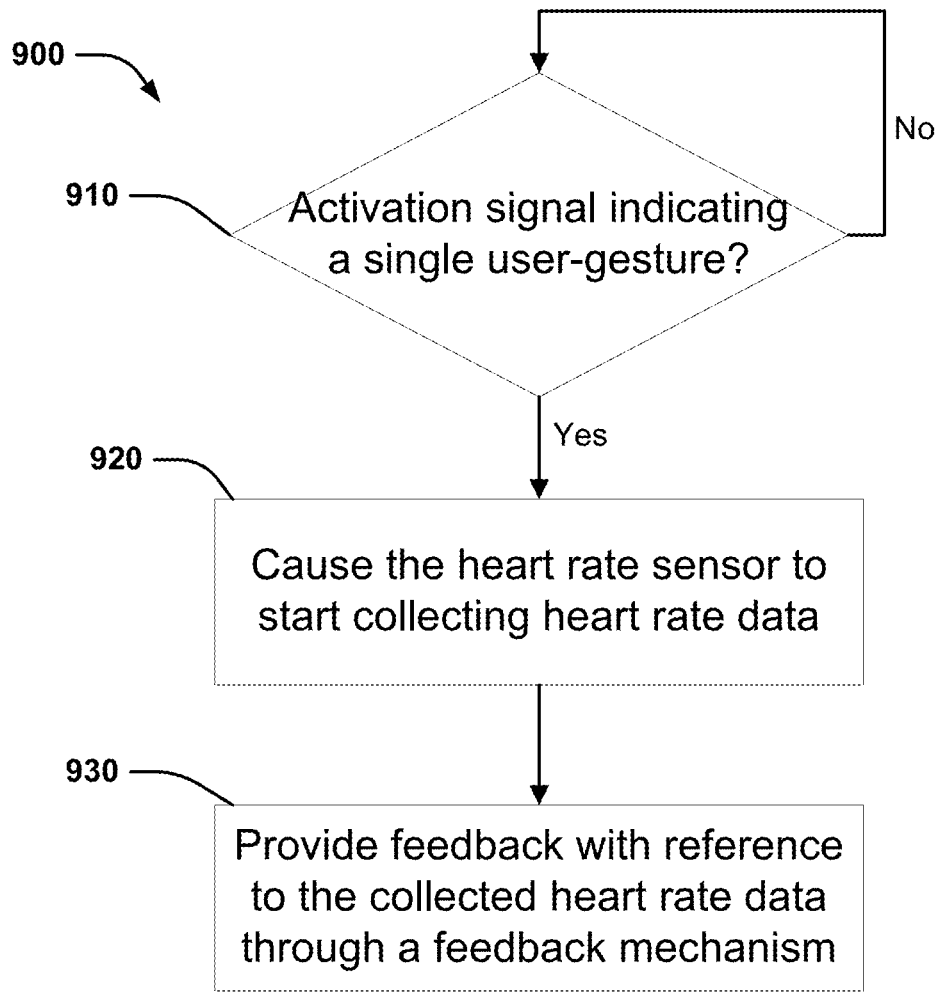
FIG. 9 depicts a flow diagram showing a process of a biometric monitoring device collecting heart rate data and providing feedback with reference to the collected heart rate data.

In some embodiments, the biometric monitoring devices use process 900 shown in the flow chart of FIG. 9 to collect heart rate data and provide feedback with reference to the collected heart rate in response to a single user-gesture. In some embodiments, the device determines if the activator receives an activation signal indicating a single user-gesture. See block 910. In some embodiments, the activation signal is collected through an activation surface area as described above. In other embodiments, the activation signal was collected by sensor without requiring an activator surface area, such as in the case of a motion sensor or electromyography sensor as described further below. Upon the activation signal, the device causes the heart rate sensor to start collecting heart rate data through the heart rate sensor surface area. See block 920. Furthermore, the device automatically provides user feedback relating to the collected heart rate data through the feedback mechanism. In some embodiments, the feedback may indicate the start, end, or failure of collecting heart rate data. In some embodiments, the feedback may include heart rate and/or related information. The feedback is provided without requiring further user-gesture in addition to the single user-gesture. See block 930.

In some embodiments, a biometric monitoring device includes one or more biometric sensors comprising an optical heart rate sensor, an activator of the heart rate sensor, a heart rate sensor surface area through which the heart rate sensor can collect heart rate data from a user, a feedback mechanism such as a display or LEDs, at least one processor, and a memory. The heart rate sensor, the activator, the feedback mechanism, the at least one processor, and the memory are communicatively connected. The memory stores computer-executable instructions for controlling the at least one processor to cause the heart rate sensor to start collecting heart rate data through the heart rate sensor surface area in response to the activator receiving an activation signal caused by a single user-gesture. The activator may be implemented as, for instance, a motion sensor that detects a defined motion pattern of the device, or touch/pressure sensor that detects a touch of a surface or a button press. The processor also provides user feedback with reference to the collected heart rate data through the feedback mechanism without requiring further user-gesture in addition to the single user-gesture. In some embodiments, the feedback may include a vibration pattern generated by a vibration motor to indicate that heart rate collection has started, ended, and/or failed.

Figure 10:
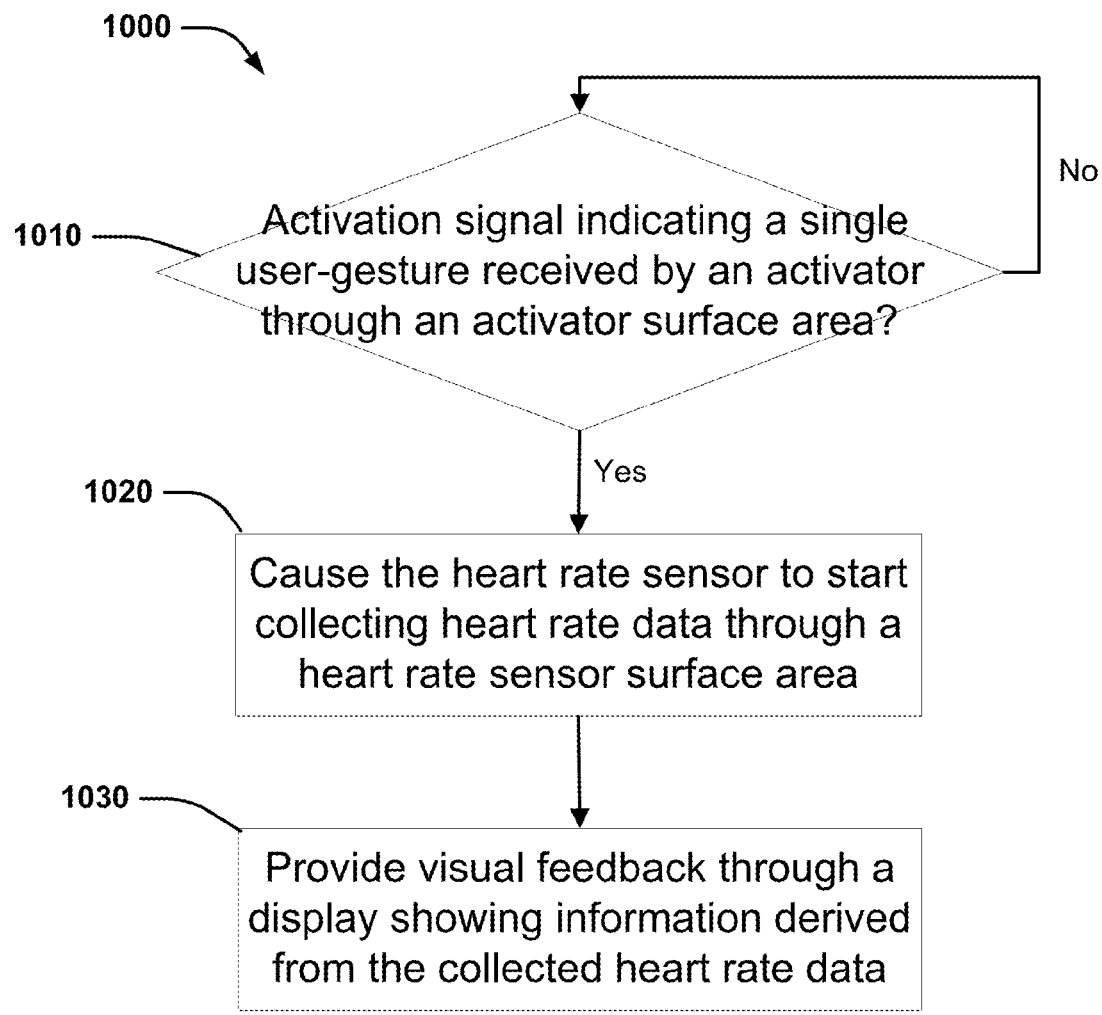
FIG. 10 depicts a flow diagram showing a process of a biometric monitoring device collecting heart rate data from the same body part that has interacted with the device to initiate data collection, and providing visual feedback showing information derived from the heart rate data.

In some embodiments, the biometric monitoring devices may use process 1000 shown in the flow chart of FIG. 10 to collect heart rate data and provide feedback with reference to the collected heart rate in response to a single user-gesture. The method 1000 is a special case of method 900, in that the activation signal is received through an actuator surface area, and that feedback is provided through a display. Therefore, the activator may be implemented as a touch or proximity sensor. In some embodiments, the device determines if the activator receives an activation signal through the activator surface area caused by a single user-gesture. See block 1010. Upon the activation signal, the device causes the heart rate sensor to start collecting heart rate data through the heart rate sensor surface area. See block 1020. Furthermore, the device automatically provides visual feedback relating to the collected heart rate data through a display. In some embodiments, providing a visual feedback through a display may comprise causing the display and/or a display backlight to turn on from an off state. In some embodiments, the feedback includes one or more of the following: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, a medical condition with reference to heart rate. The feedback is provided without requiring further user-gesture in addition to the single user-gesture. See block 1030.

In some embodiments implementing method 1000, the heart rate sensor involved is an optical sensor. In some embodiments, only one heart rate sensor surface area is required. To implement the method of 1000, a biometric monitoring device needs (i) a heart rate sensor surface area through which the heart rate sensor can collect heart rate data from a user and (ii) an activator surface area through which the activator can receive activation signals from the user, along with other components similar to the implementation of method 900. Notably, these implementations require a single user gesture to activate the heart rate sensor and to allow data collection using the sensor. Therefore some embodiments provide a closely-located or collocated hear rate sensor surface area and activator surface area, which allows a user to touch the activator surface area using a single body part, e.g., a finger, which triggers the heart rate sensor to collect data from the same body part.

Figure 11:
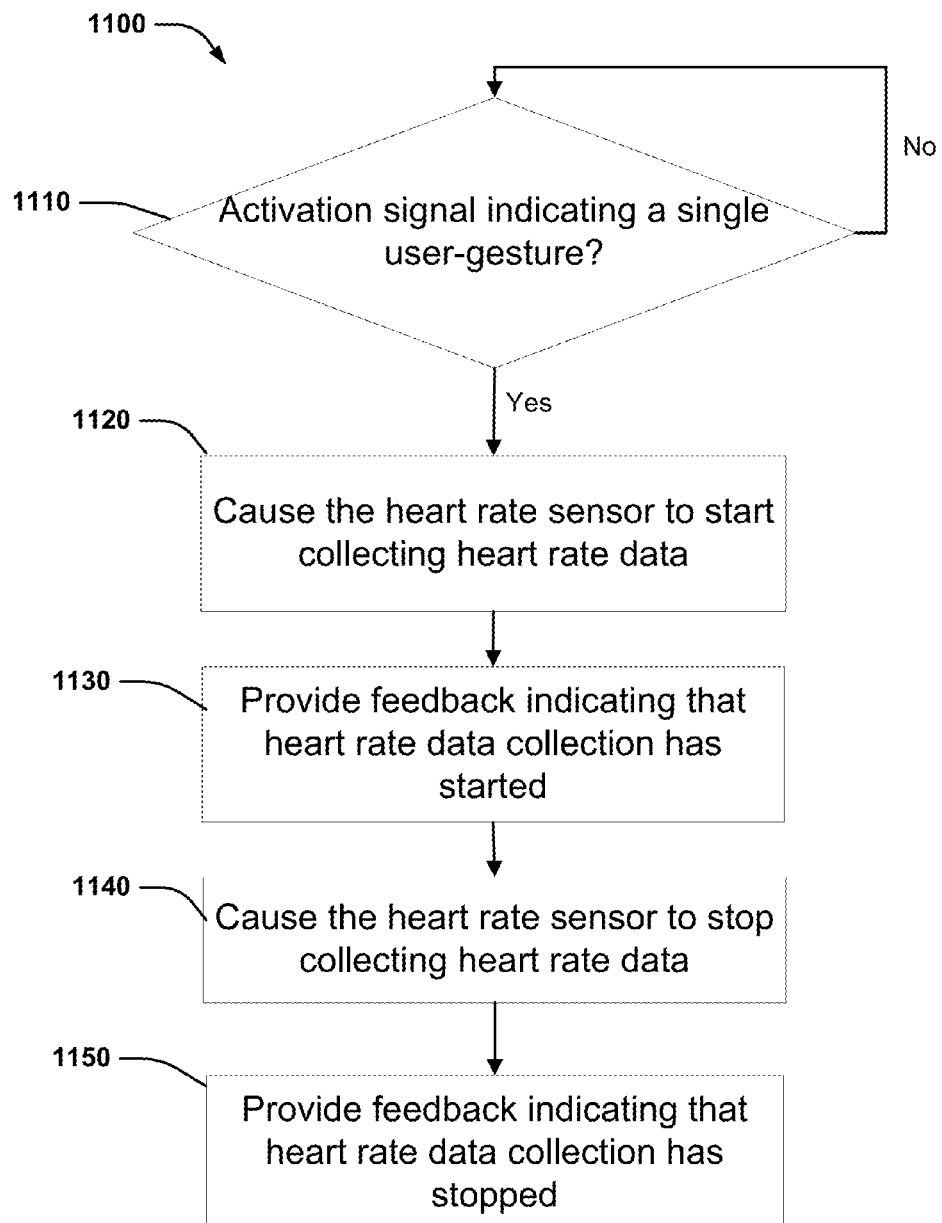
FIG. 11 depicts a flow diagram showing a process of a biometric monitoring device collecting heart rate data and providing feedback when data collection starts and stops.

In some embodiments, biometric monitoring devices may use process 1100 shown in the flow chart of FIG. 11 to collect heart rate data and provide feedback regarding the collected heart rate in response to a single user-gesture. The method 1100 is a special case of method 900, in that feedback is provided regarding the start and stop of data collection, and that heart rate sensor automatically stops. In some embodiments, the device determines if the activator receives an activation signal caused by a single user-gesture. See block 1110. Upon receiving the activation signal, the device causes the heart rate sensor to start collecting heart rate data through the heart rate sensor surface area. See block 1120. Furthermore, the device automatically provides user feedback indicating that heart rate data collection has started, e.g., by a single vibration. See block 1130. The feedback is provided without requiring further user-gesture in addition to the single user-gesture. Then the device automatically stops the heart rate sensor from collecting further data after one or more criteria are met, thereby minimizing battery consumption, block 1140. In some embodiments, the device automatically stops data collection after a set period of time, such as about 3 seconds, 5 seconds, 10 seconds, 20 seconds, 40 seconds, 1 minute, or 2 minutes. In some embodiments, the device automatically stops array data collection after a reliable heart rate reading is obtained. In some embodiments, the device further provides feedback indicating that heart rate data collection has succeeded, e.g. by a double vibration. In some embodiments, the device provides feedback indicating that heart rate data collection has failed and stopped, e.g. by a triple vibration.

In some alternative embodiments, the BMD stops or early terminates data collection in response to a new user gesture (e.g. twisting a hand wearing the BMD) or change of user gesture (lifting the finger pressing a sensor surface area). In some embodiments, the BMD provides feedback in manners that vary from the process of 1100. For instance, instead of using an active feedback to indicate a failure of data collection, the absence of feedback for a successful data collection indicates the failure of data collection. In some further embodiments, the only feedback that may be provided to the user is that a successful heart rate measurement has been obtained, e.g., no feedback is provided regarding the start of such a measurement nor of any failure of such a measurement. In one such example, the device may vibrate or emit an audible signal, e.g., a chime or beep, indicating that a heart rate measurement has been obtained in response to a user gesture.

In some embodiments, the BMD is implemented as a non-wristband form, such as a fob, pendant, beltclip, clothclip, etc. Such implementations allow user to discreetly measure heart rate, such measurement being unnoticeable by other people when measurement is taken. The implementations also afford ease of measurement, so the user does not need to run with arms crossed in front to take measurement off a wristband. For example, if the user is feeling stressed during a job interview, they may wish to obtain a measurement of their heart rate during the interview. If they have a biometric monitoring device that may be carried in their pocket, they may reach into the pocket and touch the activator of the heart rate sensor; when the heart rate sensor has obtained a valid heart rate measurement, the biometric monitoring device may gently vibrate to alert the user that the measurement has been obtained—such feedback is likely not evident to the interviewer, so there is little risk to the user that their preoccupation with their heart rate may negatively impact the interview. The non-wrist-band type of BMDs with single-gesture and discreet-feedback heart rate measurement features are suitable for measuring heart rate without interfering with current activity. For example, a user can hold the BMD in their hand while exercising and then take a quick heart rate measurement on demand without unduly interfering with the exercise activity (as compared with a wrist-mounted BMD that may require multiple body parts to contact it, or as compared with a BMD that requires that the user navigate through menus, interact with multiple points on the BMD in order to obtain a measurement (such as an EKG-based device), or utilize multiple body parts in interacting with the BMD).

In some embodiments, the BMD is implemented in a wristband form or coupled to a wrist band. Such implementation can may have the heart rate sensor on a skin-facing side (e.g., the protrusion of 614 in FIG. 6), an external side facing away from the skin when worn on the wrist (e.g. the button or touch surface of 604 in FIG. 6 or 404 in FIG. 4), or both. In an implementation that has the heart rate sensor on the skin facing side, the heart rate sensor can be activated by a specific motion pattern detected by a motion sensor. The defined motion can be implemented as different patterns, such as twisting the wrist wearing the device, shaking the device, moving the device in a "figure 8" pattern or bring the device to a watch-viewing position. Upon activation, the heart rate collects PPG data from the wrist of the user. In some embodiments, the skin-facing heart rate sensor such as that in 614 may be triggered by an activator receiving a signal indicating a single touch of a button or surface 604 facing away from the wrist skin.

In some embodiments, such as in device 400, a wrist band type BMD has a surface area 410 facing away from the wrist when worn. In some embodiments, a heart rate sensor surface area and an activator surface area are near each other or overlap, and both are located in the surface area 400. In such embodiments, a single gesture such as a touch of the surface area 410 provides an activation signal that causes the heart rate sensor to collect heart rate related signal from the same body part that has provided the activation signal.

In some embodiments, the biometric monitoring device includes a heart rate sensor and an altimeter. The device may also include an activator of the heart rate sensor, a heart rate sensor surface area through which the heart rate sensor can collect heart rate data from a user, at least one processor, and a memory. The heart rate sensor, the altimeter, the activator, the at least one processor, and the memory may be communicatively connected. The device may be configured to start collecting heart rate data through the heart rate sensor surface area in response to the activator receiving an activation signal caused by a single user-gesture. In some embodiments, the device is configured to obtain altitude data from the altimeter. In some embodiments, the altitude data comprises atmosphere pressure data or environmental pressure data, or relative changes therein. In some embodiments, the device uses the altitude data to calculate flights of stairs climbed.

In some embodiments, the biometric monitoring device includes a GPS. In some embodiments, the biometric monitoring device includes a proximity sensor. In some embodiments, the biometric monitoring device includes a heart rate sensor and an electromyography sensor. The device may cause the heart rate sensor to start collecting heart rate data through the heart rate sensor surface area in response to the electromyography sensor receiving an activation signal caused by a single user-gesture. In some such embodiments, the single user-gesture is provided by clenching the hand wearing the apparatus.

In some embodiments, the biometric monitoring device includes one or more biometric sensors comprising an optical heart rate sensor, an activator of the heart rate sensor, a heart rate sensor surface area through which the heart rate sensor can collect heart rate data from a user, a feedback mechanism, at least one processor, and a memory. The heart rate sensor, the activator, the feedback mechanism, the at least one processor, and the memory are communicatively connected. The memory stores computer-executable instructions for controlling the at least one processor to cause the heart rate sensor to start collecting heart rate data through the heart rate sensor surface area in response to the activator receiving an activation signal caused by a single user-gesture, and provide user feedback, through the feedback mechanism, with reference to the collected heart rate data without requiring further user-gesture in addition to the single user-gesture. In some embodiments, the biometric monitoring device does not have local memory. Instead, it uses a remote memory to store operation instructions.

In some embodiments, the single user-gesture consists of a user moving or interacting with the apparatus in a defined motion pattern. The activator comprises at least one sensor selected from the group consisting of: single-axis or multi-axis gyroscopes, and single-axis or multi-axis accelerometers. The device causes the heart rate sensor to start collecting heart rate data in response to a detection of the defined motion pattern using data obtained by the activator. In some embodiments, moving or interacting with the apparatus in a defined motion pattern is selected from one or more of the following: twisting the wrist wearing the apparatus, shaking the apparatus, bringing a wrist wearing the device from a resting position to a watch viewing position, moving the apparatus in a "figure 8" motion, and any combinations thereof.

In some embodiments, a user interface is communicatively connected to other components of the biometric monitoring device. In some embodiments, the user interface is included in the device itself. In other embodiments, the user interface is included in a linked smartphone, tablet, or computer. In some embodiments, the user interface comprises one or more of the following: a heart rate sensor surface area, an activator surface area, a touch screen, a display, an LED, a button, an accelerometer, a gyroscope, a finger print reader, a vibration motor, a proximity sensor, and a speaker.

In some embodiments, the heart rate sensor only collects data when the single user-gesture is occurring and from a body part of the user used to provide the single user-gesture. In some embodiments, the heart rate sensor automatically stops collecting heart rate data after a predefined time period and remains in a state that does not collect heart rate data until a new user-gesture with the activator. In some embodiments, the apparatus is configured to automatically authenticate the user based on the collected heart rate data. For example, with In some embodiments, the device include a heart rate sensor surface area and an activator surface area that are arranged on a substantially flat plane, thereby allowing a single body part of a user to simultaneously interact with the activator and the heart rate sensor. In some embodiments, the heart rate sensor surface area and the activator surface area form one continuous surface area.

In some embodiments, the apparatus includes an optical heart rate sensor for the visible light spectrum. In some embodiments, the apparatus includes an optical heart rate sensor for infrared light. In some embodiments, the apparatus includes one or more of the following: GPS, proximity sensor, gyroscope, magnetometer, accelerometer, ambient light sensor, touch screen, temperature sensor, galvanic skin response sensor, fingerprint reader, electromyography sensor, altimeter, pressure transducer, and force transducer, audio sensor, bioelectrical impedance sensor, blood pressure sensor, moisture sensor, and blood glucose sensor.

Biometric Sensors

In some embodiments, the biometric monitoring device includes a heart rate sensor that detects electrical signal generated by heart movement (e.g. electrode sensor) or an optical signal resulting from blood flow (e.g., photoplethysmography sensor or pulse oximetry sensor). In addition to heart rate data, the biometric monitoring devices discussed herein may collect one or more types of physiological and/or environmental data from sensors embedded within the biometric monitoring devices, e.g., one or more sensors selected from the group including accelerometers, gyroscopes, altimeters, etc., and/or external devices, e.g., an external blood pressure monitor, and may communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device may then transmit the data representative of the user's step count to an account on a web service, e.g., fitbit dot com, a computer, a mobile phone, or a health station where the data may be stored, processed, and visualized by the user. Indeed, the device may measure or calculate a plurality of other physiological metrics in addition to, or in place of, the user's heart rate.

The measured physiological metrics may include, but are not limited to, energy expenditure, e.g., calorie burn, floors climbed and/or descended, heart rate, heart rate variability, heart rate recovery, location and/or heading, e.g., via GPS, elevation, ambulatory speed and/or distance traveled, swimming lap count, bicycle distance and/or speed, blood pressure, blood glucose, skin conduction, skin and/or body temperature, electromyography data, electroencephalography data, weight, body fat, caloric intake, nutritional intake from food, medication intake, sleep periods, sleep phases, sleep quality and/or duration, pH levels, hydration levels, and respiration rate. The device may also measure or calculate metrics related to the environment around the user such as barometric pressure, weather conditions, e.g., temperature, humidity, pollen count, air quality, rain/snow conditions, wind speed, light exposure, e.g., ambient light, UV light exposure, time and/or duration spent in darkness, noise exposure, radiation exposure, and magnetic field. Furthermore, the biometric monitoring device, or an external system receiving data from the biometric monitoring device, may calculate metrics derived from the data collected by the biometric monitoring device. For instance, the device may derive one or more of the following from heart rate data: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate. Some of the derived information is based on both the heart rate information and other information provided by the user (e.g., age and gender) or by other sensors (elevation and skin conductance).

The biometric sensors may include one or more sensors that evaluate a physiological aspect of a wearer of the device, e.g., heart rate sensors, galvanized skin response sensors, skin temperature sensors, electromyography sensors, etc. The biometric sensors may also or alternatively include sensors that measure physical environmental characteristics that reflect how the wearer of the device is interacting with the surrounding environment, e.g., accelerometers, altimeters, GPS devices, gyroscopes, etc. All of these are biometric sensors that may all be used to gain insight into the activities of the wearer, e.g., by tracking movement, acceleration, rotations, orientation, altitude, etc.

A list of potential biometric sensor types and/or biometric data types is shown below in Table 1, including heart rate sensors. This listing is not exclusive, and other types of biometric sensors other than those listed may be used. Moreover, the data that is potentially derivable from the listed biometric sensors may also be derived, either in whole or in part, from other biometric sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

Biometric Sensors and Data (physiological and/or environmental)

| Biometric Sensor Type | Biometric data potentially measured | Potentially derivable biometric data |
| --- | --- | --- |
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation, angular velocity, angular acceleration and/or rotation | Rotation, orientation |
| Altimeters | Barometric pressure, temperature (to calculate a more accurate altitude) | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS)* | Location, elevation, speed, heading | Distance traveled, velocity/speed |
| Electromyographic Sensors | Electrical pulses | Muscle tension/extension |
| Audio Sensors | Local environmental sound levels | Laugh detection, breathing detection, snoring detection, respiration type (snoring, breathing, labored breathing, gasping), voice detection, typing detection |

TABLE 1-continued

Biometric Sensors and Data (physiological and/or environmental)

| Biometric Sensor Type | Biometric data potentially measured | Potentially derivable biometric data |
|---|---|---|
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit ARIA ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as ARIA ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

In addition to the above, some biometric data may be calculated by the biometric monitoring device without direct reference data obtained from the biometric sensors. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user and then used, in conjunction with data from an internal clock indicating the time of day, to determine how many calories have been expended by a person thus far in the day just to provide energy for basic bodily functions.

Physiological Sensors

As mentioned above, some biometric sensors can collect physiological data, others can collect environmental data, and some may collect both types of data. An optical sensor is an example of a sensor that may collect both types of data. Many of the following sensors and data overlap with the biometric sensors and data presented above. They are organized and presented below to indicate the physiological and environmental sources of information.

The biometric monitoring device of the present disclosure including a heart rate sensor may use one, some or all of the following sensors to acquire physiological data, including the physiological data outlined in Table 2 below. All combinations and permutations of physiological sensors and/or physiological data are intended to fall within the scope of the present inventions. The biometric monitoring device of the present inventions may include but is not limited to one, some or all of sensors specified below to acquire the corresponding physiological data; indeed, other type(s) of sensors may be employed to acquire the corresponding physiological data, which are intended to fall within the scope of the present inventions. Additionally, the device may derive the physiological data from the corresponding sensor output data, but is not limited to the number or types of physiological data that it could derive from said sensor.

TABLE 2

Physiological Sensors and Data

| Physiological Sensors | Physiological data acquired |
|---|---|
| Optical Reflectometer Potential embodiments: Light emitter and receiver Multi or single LED and photo diode arrangement Wavelength tuned for specific physiological signals Synchronous detection/ amplitude modulation | Heart Rate, Heart Rate Variability SpO2 (Saturation of Peripheral Oxygen) Respiration Stress Blood pressure Arterial Stiffness Blood glucose levels Blood volume Heart rate recovery Cardiac health |
| Motion Detector Potential embodiments: Inertial, Gyro or Accelerometer GPS | Activity level detection Sitting/standing detection Fall detection |
| Skin Temp | Stress |
| EMG | Muscle tension |
| EKG Potential Embodiments: 1 lead 2 lead | Heart Rate, Heart Rate Variability, Heart Rate Recovery Stress Cardiac health |
| Magnetometer | Activity level based on rotation |
| Laser Doppler | Blood flow |
| Power Meter | |
| Ultra Sound | Blood flow |
| Audio | Heart Rate, Heart Rate Variability, Heart Rate Recovery Laugh detection Respiration Respiration type - snoring, breathing, breathing problems User's voice |
| Strain gauge Potential embodiment: In a wrist band | Heart Rate, Heart Rate Variability Stress |
| Wet or Humidity sensor Potential embodiment: galvanic skin response | Stress Swimming detection Shower detection |

In one exemplary embodiment, the biometric monitoring device includes an optical sensor to detect, sense, sample, and/or generate data that may be used to determine information representative of heart rate. In addition, the optical sensor may optionally provide data for determining stress (or level thereof) and/or blood pressure of a user. In one embodiment, the biometric monitoring device includes an optical sensor having one or more light sources (LED, laser, etc.) to emit or output light into the user's body and/or light detectors (photodiodes, phototransistors, etc.) to sample, measure and/or detect a response or reflection and provide data used to determine data which is representative of heart rate (e.g., using photoplethysmography (PPG)), stress (or level thereof), and/or blood pressure of a user.

In one exemplary embodiment, a user's heart rate measurement may be triggered by activation criteria determined by one or more sensors (or processing circuitry connected to them). In this embodiment, the one or more sensors function as an activator for the heart rate sensor (i.e., the optical sensor). The criteria are based on information collected by the activator. In some embodiments in which the heart rate sensor gathers on-demand and momentary heart rate data, the activation criteria reflect a single defined user-gesture, such as moving the device in a defined motion trajectory or touching an activator surface area. In contrast, in some embodiments in which the heart rate sensor automatically gathers heart rate data without requiring a defined user gesture, when data from the motion sensor(s) indicates a period of stillness or little motion, the biometric monitoring device may trigger, acquire and/or obtain a heart rate measurement or data. In one embodiment, when the motion sensor(s) indicate user activity or motion (for example, motion that is not suitable or optimum to trigger, acquire and/or obtain desired heart rate measurement or data (for example, data used to determine a user's resting heart rate)), the biometric monitoring device and/or the sensor(s) employed to acquire and/or obtain desired heart rate measurement or data may be placed or remain in a low power state. (Note that measurements taken during motion may be less reliable and may be corrupted by motion artifacts.)

Environmental Sensors

The biometric monitoring device of the present inventions may use one, some or all of the following environmental sensors to, for example, acquire the environmental data, including environmental data outlined in Table 3 below. The biometric monitoring device is not limited to the number or types of sensors specified below but may employ other sensors that acquire environmental data outlined in the table below. All combinations and permutations of environmental sensors and/or environmental data are intended to fall within the scope of the present inventions. Additionally, the device may derive environmental data from the corresponding sensor output data, but is not limited to the types of environmental data that it could derive from said sensor.

The biometric monitoring device of the present inventions may use one or more, or all of the environmental sensors described herein and one or more, or all of the physiological sensors described herein. Indeed, biometric monitoring device of the present inventions may acquire any or all of the environmental data and physiological data described herein using any sensor now known or later developed—all of which are intended to fall within the scope of the present inventions.

TABLE 3

Environmental Sensors and Data

| Environmental Sensors | Environmental data acquired |
| --- | --- |
| Motion Detector | Location |
| Potential Embodiments: | Course |
| Inertial, Gyro or Accelerometer | Heading |
| GPS | |
| Pressure/Altimeter sensor | Elevation, elevation |
| Ambient Temp | Temperature |
| Light Sensor | Indoor vs outdoor |
| | Watching TV (spectrum/flicker rate detection) |
| | Optical data transfer - initiation, QR codes, etc. |
| | ultraviolet light exposure |
| Audio | Indoor vs. Outdoor |
| Compass | Heading |
| Potential Embodiments: | |
| 3 Axis Compass | |

In one embodiment, the biometric monitoring device may include an altimeter sensor, for example, disposed or located in the interior of the device housing. In such a case, the device housing may have a vent that allows the interior of the device to measure, detect, sample and/or experience any changes in exterior pressure. In one embodiment, the vent prevents water from entering the device while facilitating measuring, detecting and/or sampling changes in pressure via the altimeter sensor. For example, an exterior surface of the biometric monitoring device may include a vent type configuration or architecture (for example, a GORE™ vent) which allows ambient air to move in and out of the housing of the device (which allows the altimeter sensor to measure, detect and/or sample changes in pressure), but reduces, prevents and/or minimizes water and other liquids flow into the housing of the device.

The altimeter sensor, in one embodiment, may be filled with gel that allows the sensor to experience pressure changes outside of the gel. The use of a gel filled altimeter may give the device a higher level of environmental protection with or without the use of an environmentally sealed vent. The device may have a higher survivability rate with a gel filled altimeter in locations including but not limited to those that have high humidity, a clothes washer, a dish washer, a clothes dryer, a steam room, the shower, a pool, and any location where the device may be exposed to moisture, exposed to liquid or submerged in liquid.

Optical Sensors

As mentioned above, optical sensors may be used to collect both physiological (e.g., heart rate) and environmental (e.g., ambient light) data. This subsection discloses details of various embodiments of biometric monitoring devices having one or more optical sensors. In one embodiment, the optical sensors (sources and/or detectors) may be disposed on an interior or skin side of the biometric monitoring device (i.e., a side whereby the surface of the device contacts, touches and/or faces the skin of the user (hereinafter "skin side"). (See, for example, FIGS. 6-8). In another embodiment, the optical sensors may be disposed on one or more sides of the device, including the skin side and one or more sides of the device that face or are exposed to the ambient environment (environmental side). (See, for example, FIGS. 3, 4, and 6). Notably, the data from such optical sensors may be representative of physiological data and/or environmental data. Indeed, in one embodiment, the optical sensors provide, acquire and/or detect information from multiple sides of the biometric monitoring device whether or not the sensors are disposed on one or more of the multiple sides. For example, the optical sensors may obtain data related to the ambient light conditions of the environment.

Where optical sensors are disposed or arranged on the skin side of the biometric monitoring device, in operation, a light source emits light upon the skin of the user and, in response, a light detector samples, acquires and/or detects a response or reflected light from the skin (and from inside the body). The one or more sources and detectors may be arranged in an array or pattern that enhances or optimizes the SNR and/or reduces or minimizes power consumption by light sources and detectors. These optical detectors sample, acquire and/or detect physiological data which may then be processed or analyzed (for example, by resident processing circuitry) to obtain data which is representative of, for example, a user's heart rate, respiration, heart rate variability, oxygen saturation (SpO2), blood volume, blood glucose, skin moisture and skin pigmentation level.

The source(s) may emit light having one or more wavelengths which are specific or directed to a type of physiological data to be collected. The optical detectors may sample, measure and/or detect one or more wavelengths that are also specific or directed to a type of physiological data to be collected and physiological parameter (of the user) to be assessed or determined. For instance, in one embodiment, a light source emitting light having a wavelength in the green spectrum (for example, an LED that emits light having wavelengths corresponding to the green spectrum) and photodiode positioned to sample, measure and/or detect a response or reflection may provide data used to determine or detect heart rate. In contrast, a light source emitting light having a wavelength in the red spectrum (for example, an LED that emits light having wavelengths corresponding to the red spectrum) and a light source emitting light having a wavelength in the infrared spectrum (for example, an LED that emits light having wavelengths corresponding to the IR spectrum) and photodiode positioned to sample, measure and/or detect a response or reflection may provide data used to determine or detect SpO2.

Indeed, in one embodiment, the color or wavelength of the light emitted by the LED (or set of LEDs) may be modified, adjusted and/or controlled in accordance with a predetermined type of physiological data being acquired or conditions of operation. Here, the wavelength of the light emitted by the LED is adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity.

The biometric monitoring device, in one embodiment, may include a window (for example, a visually opaque window) in the housing to facilitate optical transmission between the optical sensors and the user. Here, the window may permit light (for example, of a selected wavelength) to be emitted by, for example, one or more LEDs, onto the skin of the user and a response or reflection to pass into the housing to be sampled, measured and/or detected by, for example, one or more photodiodes. In one embodiment, the circuitry related to emitting and receiving light may be disposed in the interior of the device housing and underneath a plastic or glass layer (for example, painted with infrared ink) or an infrared lens which permits infrared light to pass but not light in the human visual spectrum. In this way, the light transmission is invisible to the human eye.

Figure 12:
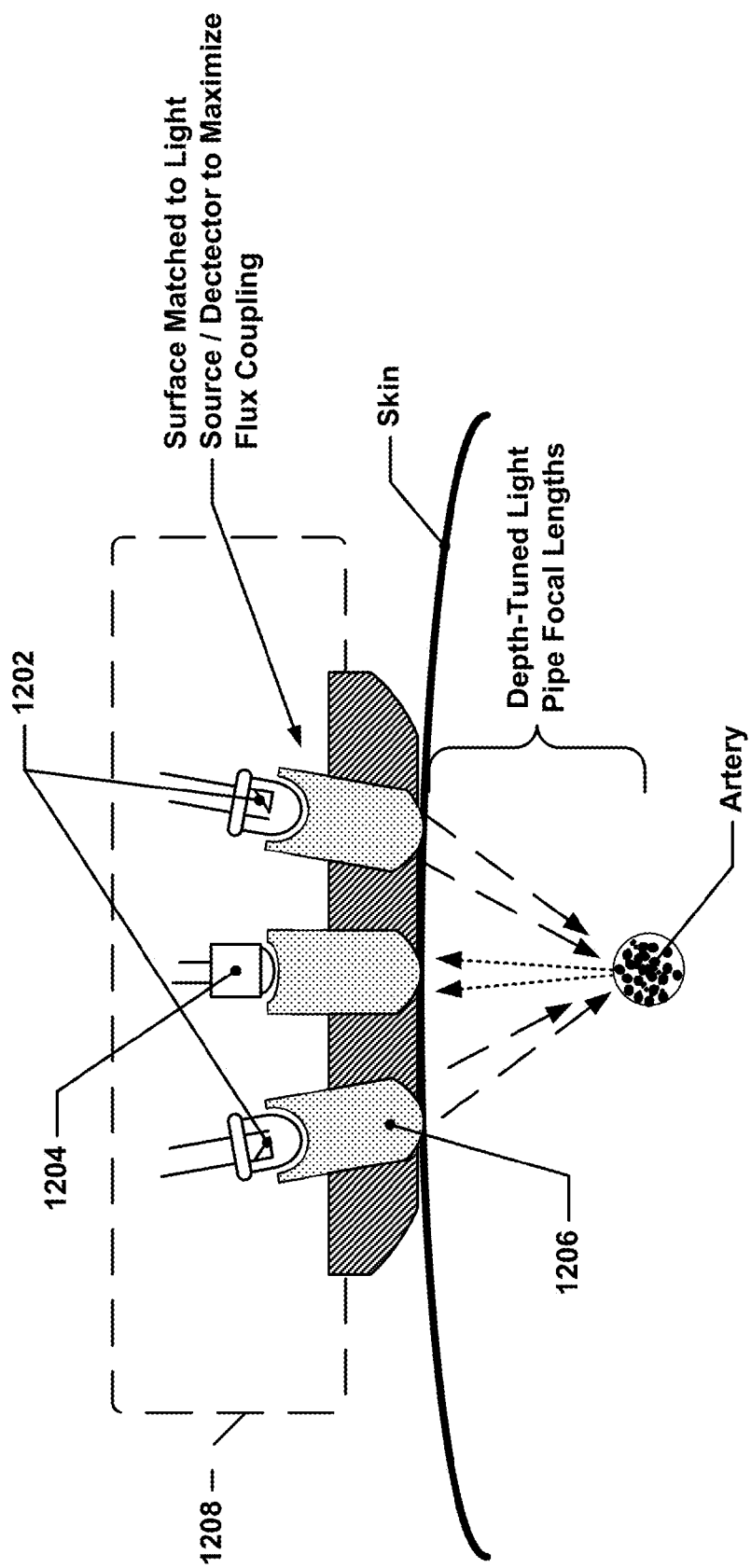
FIG. 12 illustrates an optimized PPG detector that has a protrusion with curved sides so as not to discomfort the user. Additionally, the surface of light pipes which connect the photodetector and LEDs to the user's skin are contoured to maximize light flux coupling between the LED's and photodetectors to the light pipes. The ends of the light pipes which face the user's skin are also contoured. This contour may provide focusing or defocusing to optimize the PPG signal. For example, the contour may focus light to a certain depth and location which coincides with an area where blood flow is likely to occur. Also note that the vertex of these foci overlap or are very close together so that the photodetector receives the maximum possible amount of scattered light.

The biometric monitoring device may employ light pipes or other light transmissive structures. See FIG. 12. FIG. 12 illustrates an optimized PPG detector that has a protrusion with curved sides in a watch-like housing 1208 so as not to discomfort the user wearing the device. Additionally, the surface of light pipes 1206 which permit the photodetector 1204 and LEDs 1202 to receive light from or transmit light to the user's skin are contoured to maximize light flux coupling between the LED's and photodetectors to the light pipes. The ends of the light pipes 1206 which face the user's skin are also contoured. This contour may provide focusing or defocusing to optimize the PPG signal. For example, the contour may focus light to a certain depth and location which coincides with an area where blood flow is likely to occur. Also note that the vertex of these foci overlap or are very close together so that the photodetector receives the maximum possible amount of scattered light from the tissue and artery, which provides volumetric variation indicative of heart rate and other blood related information.

In one embodiment, light is directed from the light source to the skin of the user through light pipes or other light-transmissive structures. Scattered light from the user's body may be directed back to the optical circuitry through the same or similar structures. Indeed, the transmissive structures may employ a material and/or optical design to facilitate low light loss (for example, a lens and or the use of reflective materials) thereby improving SNR of the photo detector and/or reduce power consumption of the light source(s) (light emitters and/or light detectors). In one embodiment, the light pipes or other light transmissive structures may include a material that selectively transmits light having one or more specific or predetermined wavelengths with higher efficiency than others, thereby acting as a bandpass filter. This bandpass filter may be tuned to improve the signal of a specific physiological data type. For example, in one embodiment, an In-Mold-Labeling or "IML" light transmissive structure may be implemented wherein the structure uses a material with predetermined or desired optical characteristics to create a specific bandpass characteristic, for example, to pass infrared light with greater efficiency than light of other wavelengths (for example, light having a wavelength in human visible spectrum). In another embodiment, a biometric monitoring device may employ light transmissive structure having an optically opaque portion (including certain optical properties) and an optically transparent portion (including optical properties different from the optically opaque portion). Such a structure may be provided via a double-shot or two step molding process wherein optically opaque material is injected and optically transparent material is injected. A biometric monitoring device implementing such a light transmissive structure may include different transmissive property for different wavelengths depending on the direction of light travel through the structure. For example, in one embodiment, the optically opaque material may include a property of being reflective to a specific wavelength range so as to more efficiently transport light from the light emitter(s) and from the user's body back to the skin detector (which may be of a different wavelength(s) relative to the wavelength(s) of the emitted light).

In another embodiment, reflective structures may be placed in the field of view of the light emitter(s) and/or light detector(s). For example, the sides of a hole which connects a light emitter(s) and/or light detector(s) may be covered in a reflective material (e.g. chromed). The reflective material may increase the efficiency with which the light is transported to the skin and back into the detector(s). The reflectively coasted hole may be filled in with an optical epoxy or other transparent material to prevent liquid from entering the device body.

In another embodiment which implements light transmissive structures (for example, structures created or formed through IML), such structures may include a mask consisting of an opaque material which limits the aperture of one, some or all of the light source(s) and/or detector(s). In this way, the light transmissive structures selectively "define" a preferential volume of the body that light is emitted into and/or detected from. Notably, other mask configurations may be employed or implemented in connection with the inventions described and/or illustrated herein; all such mask configurations to, for example, improve the photoplethysmography signal, and which are implemented in connection with the inventions described and/or illustrated herein, are intended to fall within the scope of the present inventions.

In another embodiment, the light emitter(s) and detector(s) may be able to transmit light through a hole or series of holes in the device exterior. This hole or series of holes may be filled in with light transmissive epoxy (e.g. optical epoxy). The epoxy would therefore form a light pipe which allows light to be transmitted from the light emitter(s) to the skin and from the skin into the light detector(s). This technique would also have the advantage that the epoxy would form a watertight seal, preventing water, sweat or other liquid from entering the device body though the hole(s) on the device exterior which allow the light emitter(s) and detector(s) to transmit and receive light from the device body exterior. An epoxy with a high thermal conductivity may be used to prevent light emitters (e.g. LED's) from overheating.

In any of the light transmissive structures described herein, the surface of the optics or device body may include a hard coat paint, hard coat dip, or optical coatings (such as anti-reflection), scratch resistance, anti-fog, and/or wavelength band block (such as ultraviolet light blocking). Such characteristics or materials may improve the operation, accuracy and/or longevity of the biometric monitoring device.

In one embodiment, the biometric monitoring device includes a concave or convex shape, on the skin side of the device, to focus light towards a specific volume at a specific depth in the skin and increase the efficiency of light collected from that point into the photodetector. (See, for example, FIG. 12). Where such a biometric monitoring device also employs light pipes to selectively and controllably route light, it may be advantageous to shape the end of the light pipe with a degree of cylindricity (for example, rather than radially symmetric). Such a configuration may improve the SNR by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's response to such emitted light (signal or data that is representative of the response to the emitted light).

In another embodiment, light transmissive epoxy may be molded into a concave or convex shape so as to provide beneficial optical properties to sensors as well. For example, during the application of light transmissive epoxy, the top of the photodetector may be shaped into a concave so light passed the optical structure would be more intense.

In addition thereto, or in lieu thereof, a portion of the skin side of the biometric monitoring device may include a friction enhancing mechanism or material. For example, the skin side of the biometric monitoring device may include a plurality of raised or depressed regions portions (for example, small bumps, ridges, grooves, and/or divots). Moreover, a friction enhancing material (for example, a gel-like material such as silicone) may be disposed on the skin side. Indeed, a device back made out of gel may also provide friction while also improving user comfort and preventing stray light from entering. As noted above, a friction enhancing mechanism or material may be used alone or in conjunction with the biometric monitoring device having a protrusion as described herein. In this regard, the biometric monitoring device may include a plurality of raised or depressed regions portions (for example, small bumps, ridges, grooves, and/or divots) in or on the protrusion portion of the device. Indeed, such raised or depressed regions portions may be incorporated/embedded in or on a window portion of the protrusion. In addition thereto, or in lieu thereof, the protrusion portion may consist of or be coated with a friction enhancing material (for example, a gel-like material such as silicone). Notably, the use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motions of the sensor relative to the user's skin during operation, especially whilst the user is in motion.

Figure 13:
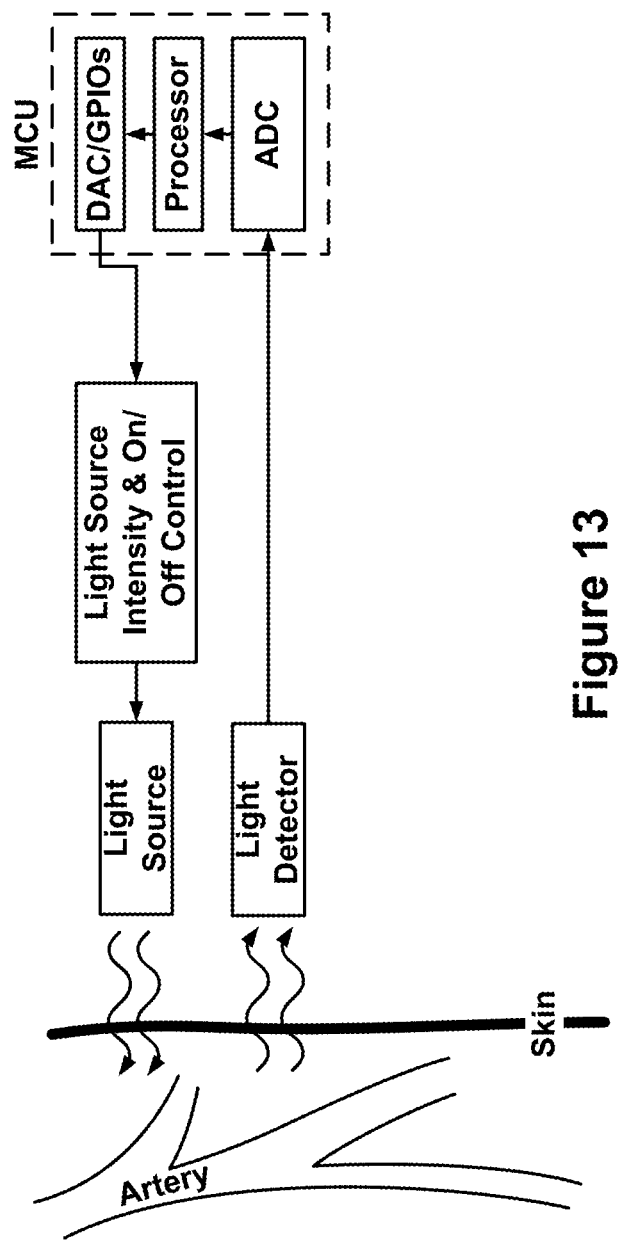
FIG. 13 illustrates a PPG sensor which has a light source, light detector, ADC, processor, DAC/GPIOs, and light source intensity and on/off control.

FIG. 13 depicts an exemplary schematic block diagram of an optical sensor where light is emitted from a light source toward the user's skin and the reflection is sensed by a light detector, which is subsequently digitized by an analog to digital converter (ADC). The digitized light sensor signal is processed by a processor of the device. The intensity of the light source may be modified (e.g., through a light source intensity control module) to maintain a desirable reflected intensity signal. For example, the light source intensity may be reduced to avoid saturation of the output signal from the light detector. As another example, the light source intensity may be increased to maintain the output signal from the light detector within a desired range of output values. Notably, the active control of the system may be achieved through linear or nonlinear control methods such as proportional-integral-derivative (PID) control, fixed step control, predictive control, neural networks, hysteresis, and the like, and may also employ additional information derived from other sensors in the device such as motion, galvanic skin response, etc. The sensor information is first processed by the processor, and then may be provided to a digital to analog converter (DAC) and/or general purpose input/output circuits (GPIOs). The processed additional information may affect a Light Source Intensity control, and/or an on/off control of the light source. FIG. 13 is provided for illustration and does not limit the implementation of such a system to, for instance, an ADC integrated within a MCU (Microcontroller Unit), or the use of a MCU for that matter. Other possible implementations include the use of one or more internal or external ADCs, FPGAs, ASICs, etc.

Figure 14:
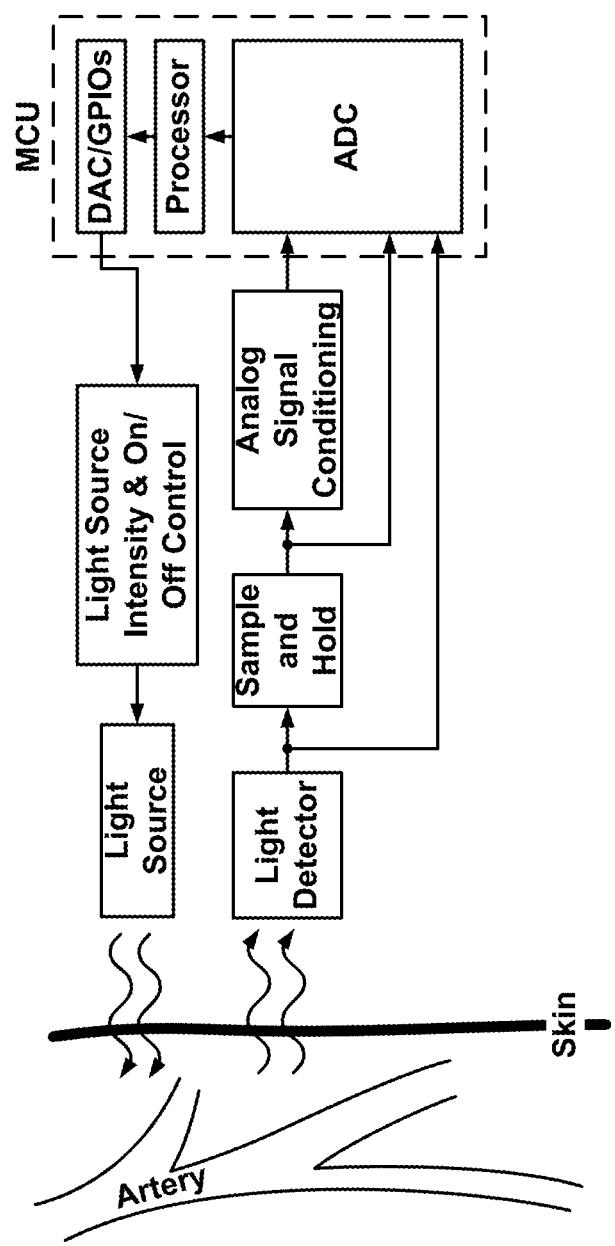
FIG. 14 illustrates a PPG sensor similar to that of FIG. 13 which additionally uses a sample and hold circuit as well as analog signal conditioning.
Figure 15:
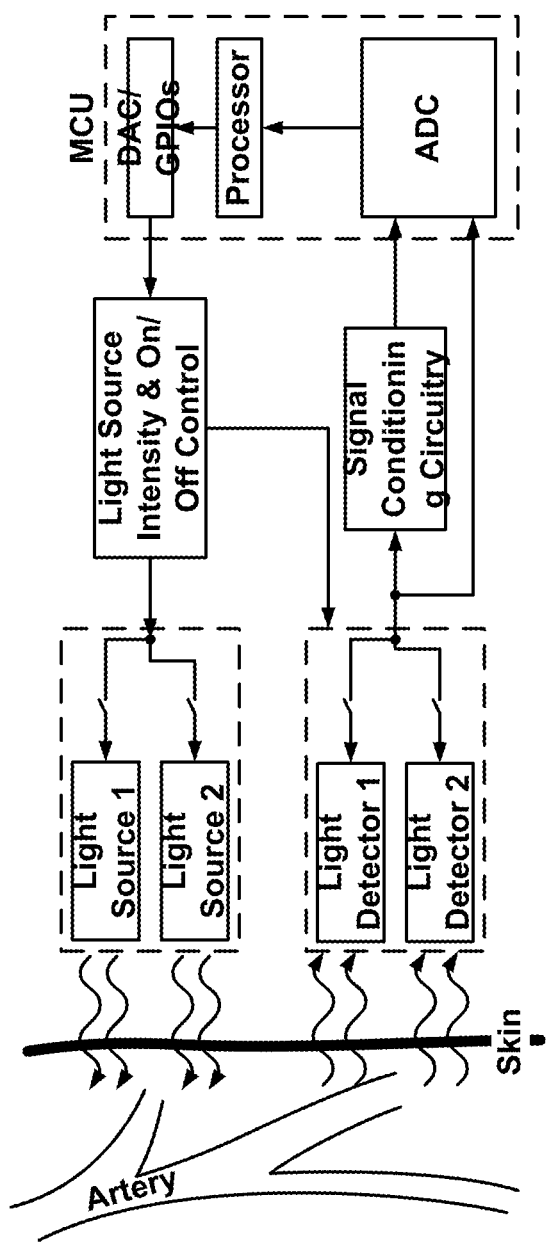
FIG. 15 illustrates a PPG having multiple switchable light sources and detectors, light source intensity/on and off control, and signal conditioning circuitry.

In another embodiment, the system may incorporate the use of a sample and hold circuit (or equivalent) to maintain the output of the light detector while the light source is turned off or attenuated to save power. See, for example, FIG. 14. In embodiments of the present disclosure where relative changes in the light detector output are of primary importance (e.g., heart rate measurement), the sample and hold circuit may not have to maintain an accurate copy of the output of the light detector. In such cases, the sample and hold may be reduced to, for example, a diode (e.g., Schottky diode) and capacitor. The output of the sample and hold may be presented to an analog signal conditioning circuit (e.g., a Sallen-Key bandpass filter, level shifter, and/or gain circuit) to condition and amplify the signal within frequency bands of interest (e.g., 0.1 Hz to 10 Hz for cardiac or respiratory function) which is then digitized by the ADC. In another embodiment shown in FIG. 15, the system includes two light sources and two light detectors, but does not include the sample and hold circuit. Similar embodiments can be implemented for a system with two or more photo sensors.

The data from sensors, which may primarily be used to obtain biometric data, may be stored in raw format by the biometric monitoring device or may be pre-processed prior to storage by the biometric monitoring device. For example, the biometric monitoring device may store or buffer the most recent 10 minutes of data in raw form but may then store data from prior to the ten-minute window as filtered data, e.g., with a lower sampling rate and/or with some form of numerical analysis, such as a moving average, performed, or as converted data, e.g., acceleration data may be converted to "steps taken," "stairs climbed," and/or "distance traveled." Data from the biometric sensors, e.g., raw data or post-processed data, may be further analyzed to determine if the biometric data is indicative of a pre-defined biometric state or condition that is associated with a user input. If such analysis indicates that such biometric data has been collected, the biometric monitoring device may then treat such an event as equivalent to a user input.

Other Components or Features

User Interface with the Device

The biometric monitoring device may include one or more mechanisms for interacting with the device either locally or remotely. In one embodiment, the biometric monitoring device may convey data visually through a digital display. The physical embodiment of this display may use any one or a plurality of display technologies including, but not limited to one or more of LED, LCD, AMOLED, E-Ink, Sharp display technology, graphical display, and other display technologies such as TN, HTN, STN, FSTN, TFT, IPS, and OLET. This display could show data acquired or stored locally on the device or could display data acquired remotely from other devices or Internet services. The device may use a sensor (for example, an Ambient Light Sensor, "ALS") to control or adjust screen backlighting. For example, in dark lighting situations, the display may be dimmed to conserve battery life, whereas in bright lighting situations, the display may increase its brightness so that it is more easily read by the user.

In another embodiment, the device may use single or multicolor LEDs to indicate a state of the device. States that the device indicate may include but are not limited to biometric states such as heart rate or application states such as an incoming message, a goal has been reached. These states may be indicated through the LED's color, being on, off, an intermediate intensity, pulsing (and/or rate thereof), and/or a pattern of light intensities from completely off to highest brightness. In one embodiment, an LED may modulate its intensity and/or color with the phase and frequency of the user's heart rate.

In one embodiment, the use of an E-Ink display would allow the display to remain on without the battery drain of a non-reflective display. This "always-on" functionality may provide a pleasant user experience in the case of, for example, a watch application where the user may simply glance at the device to see the time. The E-Ink display always displays content without comprising the battery life of the device, allowing the user to see the time as they would on a traditional watch.

The device may use a light such as an LED to display the heart rate of the user by modulating the amplitude of the light emitted at the frequency of the user's heart rate. The device may depict heart rate zones (e.g., aerobic, anaerobic) through the color of an LED (e.g., green, red) or a sequence of LEDs that light up in accordance with changes in heart rate (e.g., a progress bar). The device may be integrated or incorporated into another device or structure, for example, glasses or goggles, or communicate with glasses or goggles to display this information to the user.

The biometric monitoring device may also convey information to a user through the physical motion of the device. One such embodiment of a method to physically move the device is the use of a vibration inducing motor. The device may use this method alone, or in combination with a plurality of motion inducing technologies.

The device may convey information to a user through audio. A speaker could convey information through the use of audio tones, voice, songs, or other sounds.

These three information communication methods—visual, motion, and auditory—may be used alone or in any combination with each other or another method of communication to communicate any one or plurality of the following information:

The device has started, ended, or failed a measurement of heart rate

The user's heart rate has reached a certain level

The user has a normal, active, or resting heart rate of a specific value or in a specific range The user's heart rate has enter or exited a certain goal range or training zone The user has a new heart rate "zone" goal to reach, as in the case of heart rate zone training for running, bicycling, swimming, etc. activities User Interface with a Secondary Device In another embodiment the biometric monitoring device may transmit and receive data and/or commands to and/or from a secondary electronic device. The secondary electronic device may be in direct or indirect communication with the biometric monitoring device. Direct communication refers herein to the transmission of data between a first device and a secondary device without any intermediary devices. For example, two devices may communicate to one another over a wireless connection (e.g. Bluetooth) or a wired connection (e.g. USB). Indirect communication refers to the transmission of data between a first device and a secondary device with the aid of one or multiple intermediary third devices which relay the data. Third devices may include but are not limited to a wireless repeater (e.g. WiFi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In one embodiment, the secondary device which acts as a user interface to the biometric monitoring device may consist of a smartphone. An app on the smart phone may facilitate and/or enable the smartphone to act as a user interface to the biometric monitoring device. The biometric monitoring device may send biometric and other data to the smartphone in real-time or with some delay. The smart phone may send a command or commands to the biometric device for example to instruct it to send biometric and other data in real-time or with some delay.

The smartphone may have one or multiple apps to enable the user to view data from their biometric device or devices. The app may by default open to a "dashboard" page when the user launches or opens the app. On this page, summaries of data totals such as heart rate, the total number of steps, floors climbed miles traveled, calories burned, calories consumed and water consumed may be shown. Other pertinent information such as when the last time the app received data from the biometric monitoring device, metrics regarding the previous night's sleep (e.g. when the user went to sleep, woke up, and how long they slept for), and how many calories the user can eat in the day to maintain their caloric goals (e.g. a calorie deficit goal to enable weight loss) may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping to the left or right may enable the user to navigate through current and previous metrics.

User Gesture and Interaction

As discussed above, one or more of the biometric sensors discussed herein may be used to detect a physical gesture corresponding to a user input. This allows a user to interact with the device using physical gestures. For example, a wrist-based portable biometric device may contain an accelerometer, magnetometer (which may be used to detect the biometric monitoring device's orientation with respect to the Earth's magnetic field), and/or a gyroscope. One or more of these sensors may be used to determine when the user moves their wrist in a manner that is similar to that performed when viewing a watch. The portable biometric device may interpret this gesture as a user input or interaction. The biometric monitoring device may be configured to display the time on a display of the biometric monitoring device in response to the detection of such a gesture. Other gestures that may be used to cause the portable biometric monitoring device to display a specific data display page such as heart rate, but are not limited to, shaking the device, moving the device in a defined trajectory (e.g., a "figure 8" trajectory), multiple taps, or a specific pattern of taps. For example, a user may tap anywhere on the exterior of the portable biometric monitoring device two times within a specific time period, e.g., one second, to cause the display to show a data display page showing heart rate information.

In another embodiment, a wrist-based portable biometric device may have one or more electromyographic (EMG) sensors in device. These EMG sensors may detect when the user flexes the muscles in their forearm/wrist by forming a fist, for example. This gesture may be interpreted by the portable biometric device as a user input that causes the display to show heart rate or that triggers heart rate detection (the EMG may act as an activator for triggering heart rate detection), for example. While some physical gestures are provided here to illustrate gesture based interactions, these examples should not be considered exhaustive.

In some implementations, the portable biometric monitoring device may include mechanisms or capabilities for responding to more than one type of user interaction. User interactions may include, but are not limited to, those already disclosed herein, e.g., pressing a button, performing a gesture such as moving your hand in a manner similar to viewing a watch, tapping one or multiple times in a specific pattern, and performing a specific gesture on a touchscreen. Different kinds of user interactions may correspond to different functions. For example, a button press user interaction may cause a data display page showing a first metric related to an activity or physiological signal, e.g., ambulatory motion or cardiac signal may have the metrics step counts and heart rate respectively). An additional user input of a different input method (e.g. by tapping the device one or more times) may trigger display of a second metric related to the same activity or physiological signal. In another implementation, additional user input of a different input method may trigger presentation of a submenu or information unrelated to the previous screen shown.

A user may interact with a biometric monitoring device in one or more ways. A typical user input, for example, may include pressing a button. However, as discussed earlier in this disclosure, a user may provide input to biometric monitoring devices through other means. For example, a user may touch a virtual button on a touch screen, touch a capacitive sensor, perform a gesture on a touch screen, or perform a physical gesture, e.g., such as by moving their hand or arm in a specific way. Measurements from one or more sensors selected from the group including, but not limited to, accelerometers, galvanic skin response sensors, thermometers, pressure transducers, altimeters, gyroscopes, photoplethysmograph sensors, electromyographic (EMG) sensors, force transducers, strain gauges, and magnetometers may be used to detect user input.

In some implementations, the portable biometric monitoring device may include a motion sensor. The motion sensor may be configured to detect gestures that the user makes with the part of the body to which the biometric monitoring device is coupled. For example, the biometric monitoring device may be coupled to the user's wrist with a band. To activate the heart rate sensor, the user may twist her wrist or move her hand in a "figure 8" motion while wearing the biometric monitoring device. In another embodiment, a gesture may be performed on the device with a body part to which the device is not coupled. For example, the user may tap an activator surface area or anywhere on the housing of a biometric monitoring device worn on their forearm with a finger of the opposite hand to activate the heart rate sensor and take a heart rate measurement on the finger performing the tapping.

Figure 16:
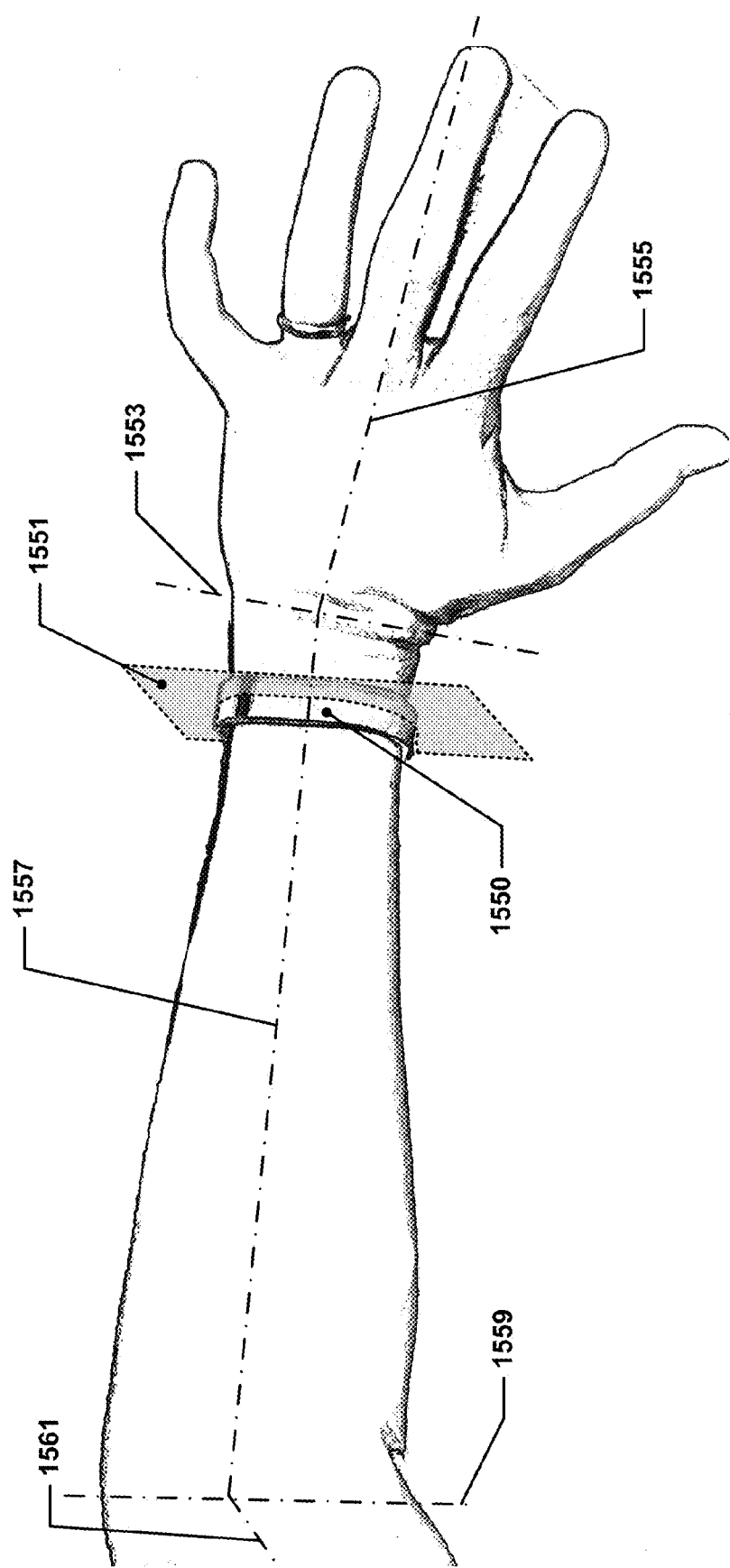
FIG. 16 depicts a person's arm, forearm, and hand with a biometric monitoring device worn on the forearm.

FIG. 16 depicts a person's arm, forearm, and hand with a biometric monitoring device worn on the forearm. In FIG. 16, a person's "arm" is shown. In everyday speech, the term "arm" is typically used to refer to the entirety of the limb connected to a person's shoulder. However, as used herein, the term "arm" refers to the portion of that limb located between the shoulder joint and the elbow joint of that limb. The term "forearm" refers to the portion of that limb between the elbow joint and the wrist joint. The forearm may encompass a portion of the limb that may often be called the "wrist," e.g., the portion of the forearm on which a person may wear a watch or bracelet. This disclosure uses the conventions outlined in Joseph E. Muscolino's "Kinesiology: The Skeletal System and Muscle Function," Second Edition (2011), when discussing various body parts or other kinesiological concepts.

Since a person's arm and forearm are organic structures with widely-varying appearances from person to person, it may be useful to utilize a common reference framework when discussing such a limb or when discussing items that may be worn on such a limb. For example, despite the wide variation in shape and size of forearms in the general population, every normal forearm will have a forearm axis 1557 that is substantially aligned with the longest dimension of the forearm. Another way of thinking of the forearm axis 1557 is as the axis that passes through the nominal centers of rotation of the wrist joint and the elbow joint. In addition to a forearm axis, it may be useful to refer to an elbow axis 1559 and a wrist axis 1553. The elbow axis 1559 may generally define the pivot axis of the forearm about the elbow joint during flexion and extension of the forearm, and the wrist axis 1553 may generally define the pivot axis of the hand about the wrist joint during flexion and extension of the hand (in reality, some of these joints are capable of complex, multi-axial rotation—the pivot axis, as used herein, refers to the axis about which the greatest extent of rotational motion is possible for a joint). An arm axis 1561 may be generally aligned with the long dimension of the arm and may pass through the center of rotation of the elbow joint and the center of rotation of the shoulder joint (not pictured). A hand axis 1555 may pass through the center of the wrist joint and generally in a direction aligned with the middle finger of the hand when at full extension.

As can be seen, the biometric monitoring device 1550 may be located in or on a wristband that encircles the forearm near the wrist (although some users may wear such bands at a loose enough setting that the band may slide over the wrist joint area itself; such bands are still considered to be configured to be worn around the wearer's forearm, however). The wristband may generally define a wristband plane 1551 that is substantially perpendicular to the forearm axis 1557.

Figure 17:
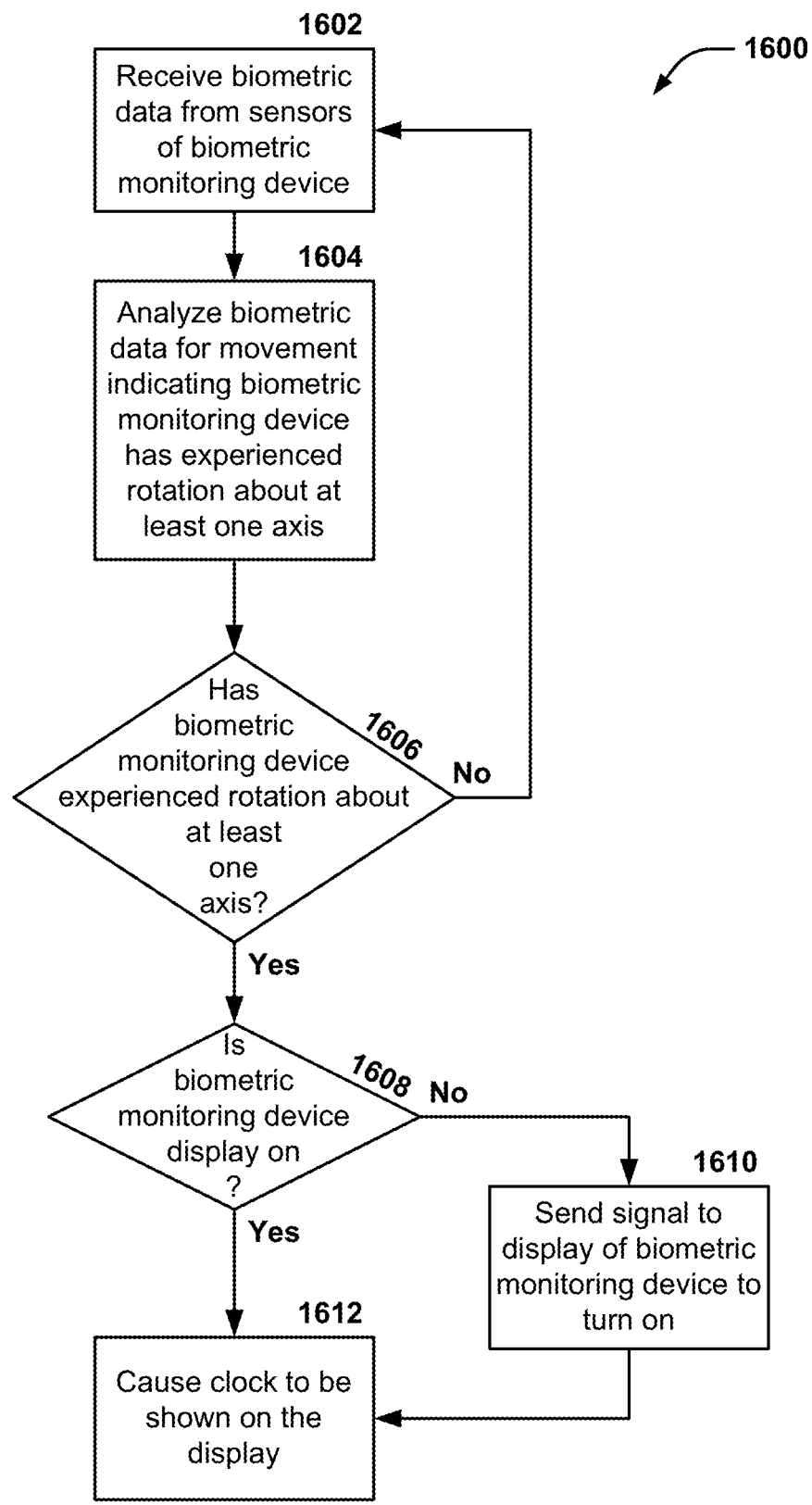
FIG. 17 depicts a flow diagram for a technique that may be used to cause a biometric monitoring device to activate the heart rate sensor responsive to data received from biometric sensors indicating motion of defined patterns.

FIG. 17 depicts a flow diagram for a technique that may be used to cause a biometric monitoring device to activate the heart rate sensor responsive to data received from biometric sensors indicating motion of defined patterns. Such motion patterns include, but not limited to, twisting the wrist wearing the device, shaking the hand wearing the device, bring a hand wearing the device from a resting position to a watch viewing position, etc. Other gestures may be used alternatively or as well.

The technique 1600 may begin in block 1602 with the receipt of data by a processor or processors of a biometric monitoring device from biometric sensors of the biometric monitoring device. Such data may be analyzed in block 1604 to determine if the biometric data indicates that the biometric monitoring device has rotated about at least one axis. For example, if the biometric data indicates that the biometric monitoring device has rotated about an axis such as the forearm axis 1557, such an indication may be interpreted as indicating that the wearer of the biometric monitoring device has rotated their wrist (and thus caused the portion of the forearm adjacent to the wrist and on which the biometric monitoring device is worn to experience similar rotation about the forearm axis). Such rotation may be detected using any of a variety of different techniques. If a gyroscope sensor is included in the biometric monitoring device, the data from such a sensor may be used to determine rotational speed and orientation of the biometric monitoring device. If accelerometers are included in the biometric monitoring device, the accelerations measured by the accelerometers may be used to calculate rotational speed and rotational orientation. For example, the Earth's gravitational field may provide a reference frame for the acceleration data that allows rotational orientation or speed based on tri-axial acceleration measurements to be calculated. Similarly, if a magnetometer is included in the biometric monitoring device, the Earth's magnetic field may be used as a reference frame to determine the absolute orientation of the biometric monitoring device relative to the Earth's surface.

In some implementations, the processor or processors of the biometric monitoring device may be configured to identify rotational movements that are more complex than simple rotation about the forearm axis. For example, when a person moves their forearm from a relaxed position, e.g., the anatomic position, to a position with the forearm generally aligned with the transverse plane and the frontal plane, such motion may involve compound rotation about an axis parallel to the elbow axis 1559 and about an axis parallel to the forearm axis 1557. In terms of an absolute coordinate system, this may translate to triaxial rotations.

In block 1606, the processor or processors of the biometric monitoring device may evaluate the biometric data to determine if the biometric monitoring device has received biometric data indicating that the biometric monitoring device has experienced rotation about at least one axis.

In some implementations, the biometric data may be further evaluated to determine if the rotational movement or orientation, if such is detected, meets certain minimum requirements. For example, the processor or processors may be further configured to determine if detected rotational movement is at least at a rate of 90°/sec and through a substantially continuous rotation of at least 45° about the forearm axis. In other implementations, the processor or processors may be further configured to determine if the detected rotational movement is at least one of the rotational rates in the group including at least 90° per second, at least 60° per second, at least 45° per second, and at least 30° per second. In such implementations, the processor or processors may also be further configured to determine if the detected angular displacement/continuous rotation is at least one angular displacement in the group including at least 90°, at least 60°, at least 45°, and at least 30°.

Such filtering may be used to eliminate spurious rotational movement that is generally classifiable as being unrelated to the motions typically experienced by a person's forearm when the person looks at a wristwatch. For example, when a person walks, they may swing their arms, which may cause the biometric sensors of a biometric monitoring device worn on the person's forearm to cyclically rotate about an axis parallel to the person's shoulder axis. Such rotation, however, would not involve rotation about the person's forearm, however, and may thus be screened out as an indicator of a watch-viewing position.

The biometric sensors used to determine whether the biometric monitoring device has experienced motion consistent with movements a person may make to bring their forearm into a watch-viewing position may be selected from a wide variety of different sensor types, including single-axis or multi-axis gyroscopes, single-axis or multi-axis accelerometers, magnetometers, electromagnetic field sensors, laser rangefinder sensors, Doppler radar sensors, and altimeter sensors. A pair of spaced-apart tri-axial accelerometers may provide a particularly cost-effective mechanism for measuring 3-dimensional movements of a biometric monitoring device, and the data collected from such sensors may be sufficient for determining whether the biometric monitoring device has experienced motion consistent with movements a person may make to bring their forearm into a watch-viewing position.

In some implementations, the determination as to whether the forearm on which the biometric monitoring device is worn has moved into a watch-viewing position may be performed using only data from accelerometers in the biometric monitoring device.

If the processor or processors determine in block 1606 that the biometric monitoring device has not experienced rotation about at least one axis, the technique may return to block 1602 and further biometric data may be received and analyzed.

If the processor or processors determine in block 1606 that the biometric monitoring device is in a watch-viewing position, then the technique may proceed to block 1608. In block 1608, the processor or processors may determine if the display of the biometric monitoring device is on or otherwise already displaying content. If not, then the processor or processors may cause the display to turn on, e.g., by sending a power-on signal to the display, in block 1610 before proceeding to block 1612. In block 1612, the processor or processors may cause a data display page showing a clock to be shown on the display. In this manner, the wearer of the biometric monitoring device need not perform any other actions to cause the display of the biometric monitoring device to show the time other than those that the wearer would generally do when checking a watch that always shows the time. This also allows the display of the biometric monitoring device to be powered off most of the time and only powered on under certain conditions, e.g., such as when the wearer "checks" their watch/biometric monitoring device.

Feedback Mechanism

The biometric monitoring device may be configured to communicate with the user through one or more feedback mechanisms, or combinations thereof, such as vibratory feedback, audio output, graphical output via a display or light-emitting devices, e.g., LEDs. For example, upon start, finish, or failure of the heart rate sensor in gathering momentary heart rate data, the biometric monitoring device may vibrate to notify the user about the different data gathering status using distinct vibration patterns. Additionally or alternatively, upon successful gathering of heart rate data, the display may turn on and present heart rate related data, e.g., averaged heart rate, heart rate target goal reached, if the goal was previously reached one or more times on a different day, week, month, or year, and/or how long it took to reach the goal, etc.

In some embodiments, the biometric monitoring device provides feedback information to users in response to a single user-gesture. The single user-gesture can be a push of a button, an activator surface area, moving the device in a defined motion pattern, etc. as described elsewhere in the disclosure.

In one implementation, the biometric monitoring device may have a display that changes what is shown, e.g., advances from one data display page to the next, after a user interaction occurs. In some embodiments, regardless of the information being displayed, the biometric monitoring device causes a heart rate sensor to start collecting heart rate data through a heart rate sensor surface area in response to an activator of the heart rate sensor receiving an activation signal caused by a single user-gesture. The device also presents the collected heart rate data or information derived therefrom on the display without requiring further user-gesture in addition to the single user-gesture. In some embodiments, the activator receives an activation signal caused by a touch of a button, a touch at a touch sensitive area, or a finger placed near a proximity sensor.

In one implementation, a specific data type or set of data types may be presented to the user with a data display page when the display first turns on. Subsequent user inputs may cause the display to advance through a succession of different data display pages, each showing different types of information. In some embodiments, if a user gesture is used to navigate between screens, there is at least one user gesture that causes the device to take an HR measurement, regardless of what screen the device is displaying.

Power Saving Feature

As mentioned previously, biometric monitoring devices are typically quite small due to practical considerations. People who wish to monitor their performance are unlikely to want to wear a large, bulky device that may interfere with their activities or that may look unsightly. As a result, biometric monitoring devices are often provided in small form factors to allow for light weight and ease of carrying. As mentioned previously, such small form factors often necessitate some design compromises. For example, there may be limited space for displays, controls, and other components of the biometric monitoring device within the device housing. One system component that may be limited in size or performance is the power source, e.g., a battery, capacitor, etc., of the biometric monitoring device. In many implementations, the biometric monitoring device may be in an "always on" state to allow it to continually collect biometric data throughout the day and night. Given that the sensors and processor(s) of the biometric monitoring device must generally remain powered to some degree in order to collect the biometric data, it may be advantageous to implement power-saving features elsewhere in the device, e.g., such as by causing the display to automatically turn off after a period of time, or by measuring certain data such as heart rate data momentarily on demand indicated by a user-gesture. A typical user gesture may be provided by pressing a button on the biometric monitoring device, flipping the biometric monitoring device over and back, or double-tapping the housing of the biometric monitoring device, touching a surface area, or placing a body part near a proximity sensor.

Generally speaking, the techniques and functions outlined above may be implemented in a biometric monitoring device as machine-readable instruction sets, either as software stored in memory, as application-specific integrated circuits, field-programmable gate-arrays, or other mechanisms for providing system control. Such instruction sets may be provided to a processor or processors of a biometric monitoring device to cause the processor or processors to control other aspects of the biometric monitoring device to provide the functionality described above.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An apparatus comprising:
one or more biometric sensors comprising a heart rate sensor;
an activator of the heart rate sensor;
a heart rate sensor surface area through which the heart rate sensor can collect heart rate data from a user;
an activator surface area through which the activator can receive activation signals from the user;
at least one processor; and
a memory,
wherein:
the one or more biometric sensors, the activator, the at least one processor, and the memory are communicatively connected, and
the memory stores computer-executable instructions for controlling the at least one processor to cause the heart rate sensor to:
start collecting heart rate data through the heart rate sensor surface area in response to the activator receiving an activation signal through the activator surface area caused by a single user-gesture; and
automatically stop collecting heart rate data when a heart rate reading of a predetermined level of heart rate data quality is obtained and remain in a state that does not collect heart rate data until another activation signal caused by a new user-gesture is received without requiring further user-gestures in addition to the single user-gesture.

2. An apparatus comprising:
one or more biometric sensors comprising an optical heart rate sensor;
an activator of the optical heart rate sensor;
a heart rate sensor surface area through which the heart rate sensor can collect heart rate data from a user;
an activator surface area through which the activator can receive activation signals from the user;
a feedback mechanism;
at least one processor; and
a memory,
wherein:
the optical heart rate sensor, the activator, the at least one processor, and the memory are communicatively connected, and the memory stores computer-executable instructions for controlling the at least one processor to:
cause the optical heart rate sensor to start collecting heart rate data through the heart rate sensor surface area in response to the activator receiving an activation signal through the activator surface area caused by a single user-gesture, and
provide user feedback, through the feedback mechanism, with reference to the collected heart rate data without requiring further user-gestures in addition to the single user-gesture.

3. The apparatus of claim 2, further comprising an altimeter communicatively connected with the heart rate sensor, the activator, the at least one processor, and the memory, wherein the memory further stores computer-executable instructions for controlling the at least one processor to obtain altitude data from the altimeter.

4. The apparatus of claim 2, wherein the heart rate sensor only collects data when the single user-gesture is occurring and only from a body part of the user used to provide the single user-gesture.

5. The apparatus of claim 4, wherein the heart rate sensor surface area and the activator surface area are arranged on a substantially flat plane, thereby allowing a single body part of a user to simultaneously interact with the activator and the heart rate sensor.

6. The apparatus of claim 2, wherein the memory further stores computer-executable instructions for controlling the at least one processor to cause the heart rate sensor to stop collecting heart rate data after a defined criterion is met without requiring further user gestures in addition to the single user-gesture.

7. The apparatus of claim 2, wherein the apparatus further comprises a vibration motor and the feedback to the user is provided as haptic vibration.

8. The apparatus of claim 2, further comprising a housing that houses at least the heart rate sensor and the activator, wherein the heart rate sensor surface area and the activator surface area are less than 1 centimeter apart as measured by the distance along the exterior surface of the housing, thereby allowing a single body part of a user to simultaneously interact with the activator and the heart rate sensor.

9. The apparatus of claim 8, wherein the heart rate sensor surface area and the activator surface area are less than 0.5 centimeters apart as measured by the distance along the exterior surface of the housing.

10. The apparatus of claim 8, wherein the heart rate sensor surface area and the activator surface area overlap along the exterior surface of the housing.

11. The apparatus of claim 8, wherein the heart rate sensor surface area is a seamless portion of the surface of the housing.

12. The apparatus of claim 8, wherein the activator surface area is a seamless portion of the surface of the housing.

13. The apparatus of claim 2, wherein the apparatus has only one heart rate sensor surface area.

14. The apparatus of claim 2, wherein the heart rate sensor surface area and the activator surface area form one continuous surface area.

15. The apparatus of claim 2, wherein the activator of the heart rate sensor is a proximity sensor.

16. The apparatus of claim 15, wherein the single user-gesture consists of the user bringing a body part into proximity with the activator surface area.

17. The apparatus of claim 2, wherein the single user-gesture consists of a touch of the activator surface area with a single body part.

18. The apparatus of claim 2, wherein the apparatus is configured to be removably attachable to a wearable accessory, and the activator surface area and heart rate sensor surface area are configured to be accessible for user interaction when attached to the wearable accessory.

19. The apparatus of claim 2, wherein the heart rate sensor, the activator, the at least one processor, and the memory are communicatively connected to a user interface on the apparatus.

20. The apparatus of claim 2, wherein the heart rate sensor, the activator, the at least one processor, and the memory are communicatively connected to a user interface on a linked smartphone, tablet, or computer.

21. The apparatus of claim 20, wherein the user interface comprises one or more of the following: the heart rate sensor surface area, the activator surface area, a touch screen, a display, an LED, a button, an accelerometer, a gyroscope, a finger print reader, a vibration motor, a proximity sensor, and a speaker.

22. A method for monitoring heart rate using a biometric monitoring device, comprising:
receiving, by an activator, an activation signal representing a single user-gesture by a user;
activating a heart rate sensor, in response to the activation signal, to start collecting heart rate data from the user;
providing user feedback, through a feedback mechanism, with reference to the collected heart rate data without requiring further user-gestures in addition to the single user-gesture; and
causing the heart rate sensor to stop collecting heart rate data when a heart rate reading of a predetermined level of heart rate data quality is obtained without requiring further user-gestures in addition to the single user-gesture.

23. The method of claim 22, wherein the heart rate sensor only collects data when the single user-gesture is occurring and from a body part of the user used to provide the single user-gesture.

24. The method of 22, wherein the user feedback provided comprises haptic vibration.

25. The method of claim 22, wherein the user feedback comprises an indication that heart rate data collection is successful.

26. The method of claim 22, wherein the user feedback comprises an indication that heart rate data collection has failed.

27. The method of claim 22, wherein the user feedback comprises one or more of the following: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate.

28. The method of 22, further comprising causing the heart rate sensor to remain in a state that does not collect heart rate data until another activation signal caused by a new user-gesture is received.

* * * * *